United States Patent
Lukyanov

(10) Patent No.: US 7,183,399 B2
(45) Date of Patent: Feb. 27, 2007

(54) NUCLEIC ACIDS ENCODING LINKED CHROMO/FLUORESCENT DOMAINS AND METHODS FOR USING THE SAME

(75) Inventor: Sergey Anatolievich Lukyanov, Moscow (RU)

(73) Assignee: Clontech Laboratories, Inc., Mountain View, CA (US)

( * ) Notice: Subject to any disclaimer, the term of this patent is extended or adjusted under 35 U.S.C. 154(b) by 0 days.

(21) Appl. No.: 10/806,930

(22) Filed: Mar. 22, 2004

(65) Prior Publication Data

US 2004/0216180 A1    Oct. 28, 2004

Related U.S. Application Data

(63) Continuation-in-part of application No. PCT/US02/32560, filed on Oct. 10, 2002, which is a continuation-in-part of application No. 09/976,673, filed on Oct. 12, 2001.

(60) Provisional application No. 60/383,336, filed on May 22, 2002, provisional application No. 60/356,225, filed on Feb. 11, 2002.

(51) Int. Cl.
  C07H 21/02    (2006.01)
  C07K 1/00    (2006.01)
  G01N 33/53    (2006.01)
(52) U.S. Cl. .................. 536/23.1; 530/350; 435/69.1
(58) Field of Classification Search ............. 536/23.1; 514/12; 530/350; 435/69.1
  See application file for complete search history.

(56) References Cited

U.S. PATENT DOCUMENTS

| | | | |
|---|---|---|---|
| 5,491,084 A | 2/1996 | Chalfie et al. | |
| 5,874,304 A | 2/1999 | Zolotukhin et al. | |
| 5,919,445 A | 7/1999 | Chao | |
| 5,958,713 A | 9/1999 | Thastrup et al. | |
| 5,968,738 A | 10/1999 | Anderson et al. | |
| 5,968,750 A | 10/1999 | Zolotukhin et al. | |
| 5,976,796 A | 11/1999 | Szalay et al. | |
| 5,985,577 A | 11/1999 | Bulinski | |
| 6,020,192 A | 2/2000 | Muzyczka et al. | |
| 6,066,476 A | 5/2000 | Tsien et al. | |
| 6,326,175 B1 * | 12/2001 | Guegler et al. | 435/91.51 |
| 6,465,199 B1 * | 10/2002 | Craig et al. | 435/7.4 |

FOREIGN PATENT DOCUMENTS

| | | |
|---|---|---|
| DE | 197 18 | 5/1997 |
| WO | WO 99/49019 | 9/1999 |
| WO | WO 00/34318 | 12/1999 |
| WO | WO 00/34319 | 12/1999 |
| WO | WO 00/34320 | 12/1999 |
| WO | WO 00/34321 | 12/1999 |
| WO | WO 00/34322 | 12/1999 |
| WO | WO 00/34323 | 12/1999 |
| WO | WO 00/34324 | 12/1999 |
| WO | WO 00/34325 | 12/1999 |
| WO | WO 00/34326 | 12/1999 |
| WO | WO 00/34526 | 12/1999 |
| WO | WO 00/22128 | 4/2000 |
| WO | WO 00/46233 | 8/2000 |
| WO | WO 01/27150 | 10/2000 |
| WO | WO 01/27150 * | 5/2001 |
| WO | WO 01/32688 | 5/2001 |
| WO | WO 01/34824 | 5/2001 |
| WO | WO 02/30965 | 4/2002 |
| WO | WO 02/48174 | 6/2002 |
| WO | WO 03/086446 | 10/2003 |

OTHER PUBLICATIONS

Bocas del Toro, Spcies Data base, Smithsonian Research Institute, striweb.si.edu/bocas_database/details.php?id=2441.*
Answers.com, definition of Oligomerization, www.answers.com/oligomerization&r=67.*
Baird et al., Biochemistry, mutagenesis, and oligomerization of DsRed, a red fluorescent protein from coral. Proc Natl Acad Sci U S A. Oct. 24, 2000;97(22):11984-9.*
Yanushevich et al. "A strategy for the generation of non-aggregating mutants of Anthozoa fluorescent proteins" FEBS Letters 511 (2002) 11-14.
Wiedemann, et al., Cracks in the β-can: Fluorescent proteins from *Anemonia sulcata* (Anthozoa, Actinaria) Proc. Nat'l Acad. Sci. (Dec. 19, 2000) 97: 14091-14096.
Ehrig et al., "Green-Fluorescent Protein Mutants with Altered Fluorescence Excitation Spectra", FEBS Letters (1995) 367: 163-166.
Anderluh et al., Biochemical and Biophysical Research Communications (1996) 220:437-442.
Dove et al., Biological Bulletin (1995) 189:288-297.
Fradkov et al., FEBS Lett. (2000) 479(3):127-30.
Gurskaya et al., FEBS Lett., (2001) 507(1):16-20.
Gurskaya et al., BMC Biochem. (2001) 2:6.
Lukyanov, K., et al (2000) J Biol Chemistry 275(34):25879-25882.
Macek et al., Eur. J. Biochem. (1995) 234:329-335.
Martynov et al., J Biol Chem. (2001) 276:21012-6.

(Continued)

Primary Examiner—Robert A. Wax
Assistant Examiner—Robert B. Mondesi
(74) Attorney, Agent, or Firm—Bret E. Field; Edward J. Baba; Bozicevic, Field & Francis LLP

(57) ABSTRACT

Nucleic acid compositions encoding polypeptide products having at least two linked chromo/fluorescent domains, as well as the proteins encoded by the same, are provided. Also provided are the polypeptides encoded by the subject nucleic acids, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

23 Claims, 12 Drawing Sheets

OTHER PUBLICATIONS

Matz, M.V., et al. (1999) *Nature Biotechnol.*, 17:969-973.
Terskikh et al., Science (2000) 290:1585-8.
Tsien, Annual Rev. of Biochemistry (1998) 67:509-544.
Tsien, Nat. Biotech. (1999) 17:956-957.
Ward et al., J. Biol. Chem. (1979) 254:781-788.
Wiedermann et al., Jarhrestagung der Deutschen Gesellschact furTropenokologie-gto. Ulm. Feb. 17-19, 1999. Poster P-4.20.
Yarbrough et al., Proc Natl Acad Sci U S A (2001) 98:462-7.
So, J.S. "Mini-Transposon Tn5gfp Constructs for Differential Tagging of Microorganisms," (1999) Biotechnology and Bioprocess Engineering, Korean Society for Biotechnology and Bioengineering, 4(2):154-156.

* cited by examiner

Figure 1
Cr-449-tandem (4-amino acid linker between monomers is in double underline).

```
  1    A CCG GTC GCC ACC ATG GTG AGC GGC CTG CTG AAG GAG AGC ATG CGC    46
  1      AgeI            M   V   S   G   L   L   K   E   S   M   R     11

47    ATC AAG ATG TAC ATG GAG GGC ACC GTG AAC GGC CAC TAC TTC AAG TGC   94
 12     I   K   M   Y   M   E   G   T   V   N   G   H   Y   F   K   C    27

95    GAG GGC GAG GGC GAC GGC AAC CCC TTC GCC GGC ACC CAG AGC ATG CGG  142
 28     E   G   E   G   D   G   N   P   F   A   G   T   Q   S   M   R    43

143    ATC CAC GTG ACC GAG GGC GCC CCC CTG CCC TTC GCC TTC GAC ATC CTG  190
 44     I   H   V   T   E   G   A   P   L   P   F   A   F   D   I   L    59

191    GCC CCC TGC TGC GAG TAC GGC AGC AGG ACC TTC GTG CAC CAC ACC GCC  238
 60     A   P   C   C   E   Y   G   S   R   T   F   V   H   H   T   A    75

239    GAG ATC CCC GAC TTC TTC AAG CAG AGC TTC CCC GAG GGC TTC ACC TGG  286
 76     E   I   P   D   F   F   K   Q   S   F   P   E   G   F   T   W    91

287    GAG AGA ACC ACC ACC TAC GAG GAC GGC GGC ATC CTG ACC GCC CAC CAG  334
 92     E   R   T   T   T   Y   E   D   G   G   I   L   T   A   H   Q   107

335    GAC ACC AGC CTG GAG GGC AAC TGC CTG ATC TAC AAG GTG AAG GTG CTG  382
108     D   T   S   L   E   G   N   C   L   I   Y   K   V   K   V   L   123

383    GGC ACC AAC TTC CCC GCC GAC GGC CCC GTG ATG AAG AAC AAG AGC GGC  430
124     G   T   N   F   P   A   D   G   P   V   M   K   N   K   S   G   139

431    GGC TGG GAG CCC AGC ACC GAG GTG GTG TAC CCC GAG AAC GGC GTG CTG  478
140     G   W   E   P   S   T   E   V   V   Y   P   E   N   G   V   L   155

479    TGC GGC CGG AAC GTG ATG GCC CTG AAG GTG GGC GAC CGG CGG CTG ATC  526
156     C   G   R   N   V   M   A   L   K   V   G   D   R   R   L   I   171

527    TGC CAC CAC TAC ACC AGC TAC CGG AGC AAG AAG GCC GTG CGG GCC CTG  574
172     C   H   H   Y   T   S   Y   R   S   K   K   A   V   R   A   L   187

575    ACC ATG CCC GGC TTC CAC TTC ACC GAC ATC CGG CTG CAG ATG CTG CGG  622
188     T   M   P   G   F   H   F   T   D   I   R   L   Q   M   L   R   203

623    AAG GAG AAG GAC GAG TAC TTC GAG CTG TAC GAG GCC AGC GTG GCC CGG  670
204     K   E   K   D   E   Y   F   E   L   Y   E   A   S   V   A   R   219

671    TAC AGC GAC CTG CCC GAG AAG GCC AAC AGA TCT CCC GGG ATG GTG AGC  718
220     Y   S   D   L   P   E   K   A   N   R   S   P   G   M   V   S   235

719    GGC CTG CTG AAG GAG AGC ATG CGC ATC AAG ATG TAC ATG GAG GGC ACC  766
236     G   L   L   K   E   S   M   R   I   K   M   Y   M   E   G   T   251

767    GTG AAC GGC CAC TAC TTC AAG TGC GAG GGC GAG GGC GAC GGC AAC CCC  814
252     V   N   G   H   Y   F   K   C   E   G   E   G   D   G   N   P   267

815    TTC GCC GGC ACC CAG AGC ATG CGG ATC CAC GTG ACC GAG GGC GCC CCC  862
268     F   A   G   T   Q   S   M   R   I   H   V   T   E   G   A   P   283

863    CTG CCC TTC GCC TTC GAC ATC CTG GCC CCC TGC TGC GAG TAC GGC AGC  910
284     L   P   F   A   F   D   I   L   A   P   C   C   E   Y   G   S   299

911    AGG ACC TTC GTG CAC CAC ACC GCC GAG ATC CCC GAC TTC TTC AAG CAG  958
300     R   T   F   V   H   H   T   A   E   I   P   D   F   F   K   Q   315

959    AGC TTC CCC GAG GGC TTC ACC TGG GAG AGA ACC ACC ACC TAC GAG GAC 1006
316     S   F   P   E   G   F   T   W   E   R   T   T   T   Y   E   D   331

1007   GGC GGC ATC CTG ACC GCC CAC CAG GAC ACC AGC CTG GAG GGC AAC TGC 1054
332     G   G   I   L   T   A   H   Q   D   T   S   L   E   G   N   C   347
```

FIGURE 1 (Cont)

```
1055  CTG ATC TAC AAG GTG AAG GTG CTG GGC ACC AAC TTC CCC GCC GAC GGC  1102
 348   L   I   Y   K   V   K   V   L   G   T   N   F   P   A   D   G    363

1103  CCC GTG ATG AAG AAC AAG AGC GGC GGC TGG GAG CCC AGC ACC GAG GTG  1150
 364   P   V   M   K   N   K   S   G   G   W   E   P   S   T   E   V    379

1151  GTG TAC CCC GAG AAC GGC GTG CTG TGC GGC CGG AAC GTG ATG GCC CTG  1198
 380   V   Y   P   E   N   G   V   L   C   G   R   N   V   M   A   L    395

1199  AAG GTG GGC GAC CGG CGG CTG ATC TGC CAC CAC TAC ACC AGC TAC CGG  1246
 396   K   V   G   D   R   R   L   I   C   H   H   Y   T   S   Y   R    411

1247  AGC AAG AAG GCC GTG CGG GCC CTG ACC ATG CCC GGC TTC CAC TTC ACC  1294
 412   S   K   K   A   V   R   A   L   T   M   P   G   F   H   F   T    427

1295  GAC ATC CGG CTG CAG ATG CTG CGG AAG GAG AAG GAC GAG TAC TTC GAG  1342
 428   D   I   R   L   Q   M   L   R   K   E   K   D   E   Y   F   E    443

1343  CTG TAC GAG GCC AGC GTG GCC CGG TAC AGC GAC CTG CCC GAG AAG GCC  1390
 444   L   Y   E   A   S   V   A   R   Y   S   D   L   P   E   K   A    459

1391  AAC TGA
 460   N   *
```

(SEQ ID NOS. 1&2)

Figure 2

Cr-449-tandem-actin (4-amino acid linker between Cr-449 monomers is noted in double underline; 4-amino acid linker between second Cr-449 and actin is noted in dashed underline).

```
   1    A CCG GTC GCC ACC ATG GTG AGC GGC CTG CTG AAG GAG AGC ATG CGC    46
   1      AgeI            M   V   S   G   L   L   K   E   S   M   R     11

47    ATC AAG ATG TAC ATG GAG GGC ACC GTG AAC GGC CAC TAC TTC AAG TGC   94
  12     I   K   M   Y   M   E   G   T   V   N   G   H   Y   F   K   C   27

95    GAG GGC GAG GGC GAC GGC AAC CCC TTC GCC GGC ACC CAG AGC ATG CGG  142
  28     E   G   E   G   D   G   N   P   F   A   G   T   Q   S   M   R   43

143    ATC CAC GTG ACC GAG GGC GCC CCC CTG CCC TTC GCC TTC GAC ATC CTG  190
  44     I   H   V   T   E   G   A   P   L   P   F   A   F   D   I   L   59

191    GCC CCC TGC TGC GAG TAC GGC AGC AGG ACC TTC GTG CAC CAC ACC GCC  238
  60     A   P   C   C   E   Y   G   S   R   T   F   V   H   H   T   A   75

239    GAG ATC CCC GAC TTC TTC AAG CAG AGC TTC CCC GAG GGC TTC ACC TGG  286
  76     E   I   P   D   F   F   K   Q   S   F   P   E   G   F   T   W   91

287    GAG AGA ACC ACC ACC TAC GAG GAC GGC GGC ATC CTG ACC GCC CAC CAG  334
  92     E   R   T   T   T   Y   E   D   G   G   I   L   T   A   H   Q  107

335    GAC ACC AGC CTG GAG GGC AAC TGC CTG ATC TAC AAG GTG AAG GTG CTG  382
 108     D   T   S   L   E   G   N   C   L   I   Y   K   V   K   V   L  123

383    GGC ACC AAC TTC CCC GCC GAC GGC CCC GTG ATG AAG AAC AAG AGC GGC  430
 124     G   T   N   F   P   A   D   G   P   V   M   K   N   K   S   G  139

431    GGC TGG GAG CCC AGC ACC GAG GTG GTG TAC CCC GAG AAC GGC GTG CTG  478
 140     G   W   E   P   S   T   E   V   V   Y   P   E   N   G   V   L  155

479    TGC GGC CGG AAC GTG ATG GCC CTG AAG GTG GGC GAC CGG CGG CTG ATC  526
 156     C   G   R   N   V   M   A   L   K   V   G   D   R   R   L   I  171

527    TGC CAC CAC TAC ACC AGC TAC CGG AGC AAG AAG GCC GTG CGG GCC CTG  574
 172     C   H   H   Y   T   S   Y   R   S   K   K   A   V   R   A   L  187

575    ACC ATG CCC GGC TTC CAC TTC ACC GAC ATC CGG CTG CAG ATG CTG CGG  622
 188     T   M   P   G   F   H   F   T   D   I   R   L   Q   M   L   R  203

623    AAG GAG AAG GAC GAG TAC TTC GAG CTG TAC GAG GCC AGC GTG GCC CGG  670
 204     K   E   K   D   E   Y   F   E   L   Y   E   A   S   V   A   R  219

671    TAC AGC GAC CTG CCC GAG AAG GCC AAC AGA TCT CCC GGG ATG GTG AGC  718
 220     Y   S   D   L   P   E   K   A   N   R   S   P   G   M   V   S  235

719    GGC CTG CTG AAG GAG AGC ATG CGC ATC AAG ATG TAC ATG GAG GGC ACC  766
 236     G   L   L   K   E   S   M   R   I   K   M   Y   M   E   G   T  251

767    GTG AAC GGC CAC TAC TTC AAG TGC GAG GGC GAG GGC GAC GGC AAC CCC  814
 252     V   N   G   H   Y   F   K   C   E   G   E   G   D   G   N   P  267

815    TTC GCC GGC ACC CAG AGC ATG CGG ATC CAC GTG ACC GAG GGC GCC CCC  862
 268     F   A   G   T   Q   S   M   R   I   H   V   T   E   G   A   P  283

863    CTG CCC TTC GCC TTC GAC ATC CTG GCC CCC TGC TGC GAG TAC GGC AGC  910
 284     L   P   F   A   F   D   I   L   A   P   C   C   E   Y   G   S  299

911    AGG ACC TTC GTG CAC CAC ACC GCC GAG ATC CCC GAC TTC TTC AAG CAG  958
 300     R   T   F   V   H   H   T   A   E   I   P   D   F   F   K   Q  315

959    AGC TTC CCC GAG GGC TTC ACC TGG GAG AGA ACC ACC ACC TAC GAG GAC 1006
 316     S   F   P   E   G   F   T   W   E   R   T   T   T   Y   E   D  331
```

FIGURE 2 (CONT)

```
1007  GGC GGC ATC CTG ACC GCC CAC CAG GAC ACC AGC CTG GAG GGC AAC TGC  1054
332    G   G   I   L   T   A   H   Q   D   T   S   L   E   G   N   C   347

1055  CTG ATC TAC AAG GTG AAG GTG CTG GGC ACC AAC TTC CCC GCC GAC GGC  1102
348    L   I   Y   K   V   K   V   L   G   T   N   F   P   A   D   G   363

1103  CCC GTG ATG AAG AAC AAG AGC GGC GGC TGG GAG CCC AGC ACC GAG GTG  1150
364    P   V   M   K   N   K   S   G   G   W   E   P   S   T   E   V   379

1151  GTG TAC CCC GAG AAC GGC GTG CTG TGC GGC CGG AAC GTG ATG GCC CTG  1198
380    V   Y   P   E   N   G   V   L   C   G   R   N   V   M   A   L   395

1199  AAG GTG GGC GAC CGG CGG CTG ATC TGC CAC CAC TAC ACC AGC TAC CGG  1246
396    K   V   G   D   R   R   L   I   C   H   H   Y   T   S   Y   R   411

1247  AGC AAG AAG GCC GTG CGG GCC CTG ACC ATG CCC GGC TTC CAC TTC ACC  1294
412    S   K   K   A   V   R   A   L   T   M   P   G   F   H   F   T   427

1295  GAC ATC CGG CTG CAG ATG CTG CGG AAG GAG AAG GAC GAG TAC TTC GAG  1342
428    D   I   R   L   Q   M   L   R   K   E   K   D   E   Y   F   E   443

1343  CTG TAC GAG GCC AGC GTG GCC CGG TAC AGC GAC CTG CCC GAG AAG GCC  1390
444    L   Y   E   A   S   V   A   R   Y   S   D   L   P   E   K   A   459

1391  AAC AGA ACT CGA GCT ATG GAT GAT GAT ATC GCC G...                  1424
460    N   R   T   R   A   M   D   D   D   I   A...                    470
                               actin
```
(SEQ ID NOs. 3&4).

FIGURE 3

HcRed-cr-1 tandem (4-amino acid linker between monomers is in double underline).

```
               ATGTCTGGTTTGTTGAAAGAAAGTATGCGCATCAAGATGTACAT
                M  S  G  L  L  K  E  S  M  R  I  K  M  Y  M

GGAAGGCACGGTTAATGGCCATTATTTCAAGTGTGAAGGAGAGGGAGACGGCAACCCATT
 E  G  T  V  N  G  H  Y  F  K  C  E  G  E  G  D  G  N  P  F

TGCAGGTACGCAGAGCATGAGGATTCATGTCACCGAAGGGGCTCCATTACCATTTGCCTT
 A  G  T  Q  S  M  R  I  H  V  T  E  G  A  P  L  P  F  A  F

CGACATTTTGGCACCGTGTTGTGAGTACGGCAGCAGGACCTTTGTCCACCATACGGCAGA
 D  I  L  A  P  C  C  E  Y  G  S  R  T  F  V  H  H  T  A  E

GATTCCCGATTTCTTCAAGCAGTCTTTCCCTGAAGGCTTTACTTGGGAAAGAACCACAAC
 I  P  D  F  F  K  Q  S  F  P  E  G  F  T  W  E  R  T  T  T

CTATGAAGATGGAGGCATTCTTACTGCTCATCAGGACACAAGCCTGGAGGGGAACTGCCT
 Y  E  D  G  G  I  L  T  A  H  Q  D  T  S  L  E  G  N  C  L

TATATACAAGGTGAAAGTCCATGGTACCAATTTTCCTGCTGATGGCCCCGTGATGAAGAA
 I  Y  K  V  K  V  H  G  T  N  F  P  A  D  G  P  V  M  K  N

CAAATCAGGAGGATGGGAGCCAAGCACTGAGGTGGTTTATCCAGAGAATGGTGTCCTGTG
 K  S  G  G  W  E  P  S  T  E  V  V  Y  P  E  N  G  V  L  C

TGGACGTAATGTGATGGCCCTTAAAGTCGGTGATCGTCATTTGATCTGCCATCACTATAC
 G  R  N  V  M  A  L  K  V  G  D  R  H  L  I  C  H  H  Y  T

TTCTTACAGGTCCAAGAAAGCAGTCCGTGCCTTGACAATGCCAGGATTTCATTTTACAGA
 S  Y  R  S  K  K  A  V  R  A  L  T  M  P  G  F  H  F  T  D

CATCCGCCTTCAGATGCTGAGGAAAAAGAAAGACGAGTACTTTGAACTGTACGAAGCATC
 I  R  L  Q  M  L  R  K  K  K  D  E  Y  F  E  L  Y  E  A  S

TGTGGCTAGGTACAGTGATCTTCCTGAAAAAGCAAAAGA TCT CCC GGG
 V  A  R  Y  S  D  L  P  E  K  A  N  R   S   P   G

ATGTCTGGTTTGTTGAAAGAAAGTATGCGCATCAAGATGTACAT
 M  S  G  L  L  K  E  S  M  R  I  K  M  Y  M

GGAAGGCACGGTTAATGGCCATTATTTCAAGTGTGAAGGAGAGGGAGACGGCAACCCATT
 E  G  T  V  N  G  H  Y  F  K  C  E  G  E  G  D  G  N  P  F

TGCAGGTACGCAGAGCATGAGGATTCATGTCACCGAAGGGGCTCCATTACCATTTGCCTT
 A  G  T  Q  S  M  R  I  H  V  T  E  G  A  P  L  P  F  A  F

CGACATTTTGGCACCGTGTTGTGAGTACGGCAGCAGGACCTTTGTCCACCATACGGCAGA
 D  I  L  A  P  C  C  E  Y  G  S  R  T  F  V  H  H  T  A  E

GATTCCCGATTTCTTCAAGCAGTCTTTCCCTGAAGGCTTTACTTGGGAAAGAACCACAAC
 I  P  D  F  F  K  Q  S  F  P  E  G  F  T  W  E  R  T  T  T

CTATGAAGATGGAGGCATTCTTACTGCTCATCAGGACACAAGCCTGGAGGGGAACTGCCT
 Y  E  D  G  G  I  L  T  A  H  Q  D  T  S  L  E  G  N  C  L

TATATACAAGGTGAAAGTCCATGGTACCAATTTTCCTGCTGATGGCCCCGTGATGAAGAA
 I  Y  K  V  K  V  H  G  T  N  F  P  A  D  G  P  V  M  K  N

CAAATCAGGAGGATGGGAGCCAAGCACTGAGGTGGTTTATCCAGAGAATGGTGTCCTGTG
 K  S  G  G  W  E  P  S  T  E  V  V  Y  P  E  N  G  V  L  C

TGGACGTAATGTGATGGCCCTTAAAGTCGGTGATCGTCATTTGATCTGCCATCACTATAC
 G  R  N  V  M  A  L  K  V  G  D  R  H  L  I  C  H  H  Y  T

TTCTTACAGGTCCAAGAAAGCAGTCCGTGCCTTGACAATGCCAGGATTTCATTTTACAGA
 S  Y  R  S  K  K  A  V  R  A  L  T  M  P  G  F  H  F  T  D
```

FIGURE 3 (CONT)

```
CATCCGCCTTCAGATGCTGAGGAAAAAGAAAGACGAGTACTTTGAACTGTACGAAGCATC
 I   R   L   Q   M   L   R   K   K   K   D   E   Y   F   E   L   Y   E   A   S

TGTGGCTAGGTACAGTGATCTTCCTGAAAAAGCAAATTGA
 V   A   R   Y   S   D   L   P   E   K   A   N   *
```

(SEQ ID NOS. 5 & 6)

FIGURE 4.     AsRed-35-5NA tandem

```
    ATG GCC TCC CTG CTG ACC GAG ACC ATG CCC TTC AGG ACC ACC ATC
     M   A   S   L   L   T   E   T   M   P   F   R   T   T   I

GAG GGC ACC GTG AAC GGC CAC TAC TTC AAG TGC ACC GGC AAG GGC GAG
 E   G   T   V   N   G   H   Y   F   K   C   T   G   K   G   E

GGC AAC CCC CTC GAG GGC ACC CAG GAG ATG AAG ATC GAG GTG ATC GAG
 G   N   P   L   E   G   T   Q   E   M   K   I   E   V   I   E

GGC GGC CCC CTG CCC TTC GCC TTC CAC ATC CTG TCC ACC TCC TGC ATG
 G   G   P   L   P   F   A   F   H   I   L   S   T   S   C   M

TAC GGC TCC AAG GCC TTC ATC AAG TAC GTG TCC GGC ATC CCC GAC TAC
 Y   G   S   K   A   F   I   K   Y   V   S   G   I   P   D   Y

TTC AAG CAG TCC CTC CCC GAG GGC TTC ACC TGG GAG CGC ACC ACC ACC
 F   K   Q   S   L   P   E   G   F   T   W   E   R   T   T   T

TAC GAG GAC GGC GGC TTC CTG ACC GCC CAC CAG GAC ACC TCC CTG GAC
 Y   E   D   G   G   F   L   T   A   H   Q   D   T   S   L   D

GGC GAC TGC CTG GTG TAC AAG GTG AAG ATC CTG GGC AAC AAC TTC CCC
 G   D   C   L   V   Y   K   V   K   I   L   G   N   N   F   P

GCC GAC GGC CCC GTG ATG CAG AAC AAG GCC GGC CGC TGG GAG CCC TCC
 A   D   G   P   V   M   Q   N   K   A   G   R   W   E   P   S

ACC GAG ATC GTG TAC GAG GTG GAC GGC GTG CTG CGC GGC CAG TCC AGC
 T   E   I   V   Y   E   V   D   G   V   L   R   G   Q   S   S

ATG GCC CTG GAG TGC CCC GGC GGT CGC CAC CTG ACC TGC CAC CTG CAC
 M   A   L   E   C   P   G   G   R   H   L   T   C   H   L   H

ACC ACC TAC CGC TCC AAG AAG CCC GCC TCC GCC CTG AAG ATG CCC GGC
 T   T   Y   R   S   K   K   P   A   S   A   L   K   M   P   G

TTC CAC TTC GAG GAC CAC CGC ATC GAG ATC CTG GAG GAG GTG GAG AAG
 F   H   F   E   D   H   R   I   E   I   L   E   E   V   E   K

GGC AAG TGC TAC AAG CAG TAC GAG GCC GCC GTG GGC CGC TAC TGC GAC
 G   K   C   Y   K   Q   Y   E   A   A   V   G   R   Y   C   D

GCC GCC CCC TCC AAG CTG GGC CAC AAC AGA TCT CCC GGG
 A   A   P   S   K   L   G   H   N   R   S   P   G

ATG GCC TCC CTG CTG ACC GAG ACC ATG CCC TTC AGG ACC ACC ATC
     M   A   S   L   L   T   E   T   M   P   F   R   T   T   I

GAG GGC ACC GTG AAC GGC CAC TAC TTC AAG TGC ACC GGC AAG GGC GAG
 E   G   T   V   N   G   H   Y   F   K   C   T   G   K   G   E

GGC AAC CCC CTC GAG GGC ACC CAG GAG ATG AAG ATC GAG GTG ATC GAG
 G   N   P   L   E   G   T   Q   E   M   K   I   E   V   I   E

GGC GGC CCC CTG CCC TTC GCC TTC CAC ATC CTG TCC ACC TCC TGC ATG
 G   G   P   L   P   F   A   F   H   I   L   S   T   S   C   M

TAC GGC TCC AAG GCC TTC ATC AAG TAC GTG TCC GGC ATC CCC GAC TAC
 Y   G   S   K   A   F   I   K   Y   V   S   G   I   P   D   Y

TTC AAG CAG TCC CTC CCC GAG GGC TTC ACC TGG GAG CGC ACC ACC ACC
 F   K   Q   S   L   P   E   G   F   T   W   E   R   T   T   T

TAC GAG GAC GGC GGC TTC CTG ACC GCC CAC CAG GAC ACC TCC CTG GAC
 Y   E   D   G   G   F   L   T   A   H   Q   D   T   S   L   D
```

Figure 4 (Cont)

```
GGC GAC TGC CTG GTG TAC AAG GTG AAG ATC CTG GGC AAC AAC TTC CCC
 G   D   C   L   V   Y   K   V   K   I   L   G   N   N   F   P

GCC GAC GGC CCC GTG ATG CAG AAC AAG GCC GGC CGC TGG GAG CCC TCC
 A   D   G   P   V   M   Q   N   K   A   G   R   W   E   P   S

ACC GAG ATC GTG TAC GAG GTG GAC GGC GTG CTG CGC GGC CAG TCC AGC
 T   E   I   V   Y   E   V   D   G   V   L   R   G   Q   S   S

ATG GCC CTG GAG TGC CCC GGC GGT CGC CAC CTG ACC TGC CAC CTG CAC
 M   A   L   E   C   P   G   G   R   H   L   T   C   H   L   H

ACC ACC TAC CGC TCC AAG AAG CCC GCC TCC GCC CTG AAG ATG CCC GGC
 T   T   Y   R   S   K   K   P   A   S   A   L   K   M   P   G

TTC CAC TTC GAG GAC CAC CGC ATC GAG ATC CTG GAG GAG GTG GAG AAG
 F   H   F   E   D   H   R   I   E   I   L   E   E   V   E   K

GGC AAG TGC TAC AAG CAG TAC GAG GCC GCC GTG GGC CGC TAC TGC GAC
 G   K   C   Y   K   Q   Y   E   A   A   V   G   R   Y   C   D

GCC GCC CCC TCC AAG CTG GGC CAC AAC
 A   A   P   S   K   L   G   H   N
```

(SEQ ID NOS: 7 & 8)

FIGURE 5. AsRed-35-5D tandem

```
GCC TCC CTG CTG ACC GAG ACC ATG CCC TTC AGG ACC ACC ATC
 A   S   L   L   T   E   T   M   P   F   R   T   T   I

GAG GGC ACC GTG AAC GGC CAC TAC TTC AAG TGC ACC GGC AAG GGC GAG
 E   G   T   V   N   G   H   Y   F   K   C   T   G   K   G   E

GGC AAC CCC CTC GAG GGC ACC CAG GAG ATG AAG ATC GAG GTG ATC GAG
 G   N   P   L   E   G   T   Q   E   M   K   I   E   V   I   E

GGC GGC CCC CTG CCC TTC GCC TTC CAC ATC CTG TCC ACC TCC TGC ATG
 G   G   P   L   P   F   A   F   H   I   L   S   T   S   C   M

TAC GGC TCC AAG GCC TTC ATC AAG TAC GTG TCC GGC ATC CCC GAC TAC
 Y   G   S   K   A   F   I   K   Y   V   S   G   I   P   D   Y

TTC AAG CAG TCC CTC CCC GAG GGC TTC ACC TGG GAG CGC ACC ACC ACC
 F   K   Q   S   L   P   E   G   F   T   W   E   R   T   T   T

TAC GAG GAC GGC GGC TTC CTG ACC GCC CAC CAG GAC ACC TCC CTG GAC
 Y   E   D   G   G   F   L   T   A   H   Q   D   T   S   L   D

GGC GAC TGC CTG GTG TAC AAG GTG AAG ATC CTG GGC AAC AAC TTC CCC
 G   D   C   L   V   Y   K   V   K   I   L   G   N   N   F   P

GCC GAC GGC CCC GTG ATG CAG AAC AAG GCC GGC CGC TGG GAG CCC TCC
 A   D   G   P   V   M   Q   N   K   A   G   R   W   E   P   S

ACC GAG ATC GTG TAC GAG GTG GAC GGC GTG CTG CGC GGC CAG TCC CTG
 T   E   I   V   Y   E   V   D   G   V   L   R   G   Q   S   L

ATG GCC CTG GAG TGC CCC GGC GGT CGC CAC CTG ACC TGC CAC CTG CAC
 M   A   L   E   C   P   G   G   R   H   L   T   C   H   L   H

ACC ACC TAC CGC TCC AAG AAG CCC GCC TCC GCC CTG AAG ATG CCC GGC
 T   T   Y   R   S   K   K   P   A   S   A   L   K   M   P   G

TTC CAC TTC GAG GAC CAC CGC ATC GAG ATC CTG GAG GAG GTG GAG AAG
 F   H   F   E   D   H   R   I   E   I   L   E   E   V   E   K

GGC AAG TGC TAC AAG CAG TAC GAG GCC GCC GTG GGC CGC TAC TGC GAC
 G   K   C   Y   K   Q   Y   E   A   A   V   G   R   Y   C   D

GCC GCC CCC TCC AAG CTG GGC CAC AAC AGA TCT CCC GGG
 A   A   P   S   K   L   G   H   N   R   S   P   G

GCC TCC CTG CTG ACC GAG ACC ATG CCC TTC AGG ACC ACC ATC
     A   S   L   L   T   E   T   M   P   F   R   T   T   I

GAG GGC ACC GTG AAC GGC CAC TAC TTC AAG TGC ACC GGC AAG GGC GAG
 E   G   T   V   N   G   H   Y   F   K   C   T   G   K   G   E

GGC AAC CCC CTC GAG GGC ACC CAG GAG ATG AAG ATC GAG GTG ATC GAG
 G   N   P   L   E   G   T   Q   E   M   K   I   E   V   I   E

GGC GGC CCC CTG CCC TTC GCC TTC CAC ATC CTG TCC ACC TCC TGC ATG
 G   G   P   L   P   F   A   F   H   I   L   S   T   S   C   M

TAC GGC TCC AAG GCC TTC ATC AAG TAC GTG TCC GGC ATC CCC GAC TAC
 Y   G   S   K   A   F   I   K   Y   V   S   G   I   P   D   Y

TTC AAG CAG TCC CTC CCC GAG GGC TTC ACC TGG GAG CGC ACC ACC ACC
'F   K   Q   S   L   P   E   G   F   T   W   E   R   T   T   T

TAC GAG GAC GGC GGC TTC CTG ACC GCC CAC CAG GAC ACC TCC CTG GAC
 Y   E   D   G   G   F   L   T   A   H   Q   D   T   S   L   D
```

FIGURE 5 (CONT)

```
GGC GAC TGC CTG GTG TAC AAG GTG AAG ATC CTG GGC AAC AAC TTC CCC
 G   D   C   L   V   Y   K   V   K   I   L   G   N   N   F   P

GCC GAC GGC CCC GTG ATG CAG AAC AAG GCC GGC CGC TGG GAG CCC TCC
 A   D   G   P   V   M   Q   N   K   A   G   R   W   E   P   S

ACC GAG ATC GTG TAC GAG GTG GAC GGC GTG CTG CGC GGC CAG TCC CTG
 T   E   I   V   Y   E   V   D   G   V   L   R   G   Q   S   L

ATG GCC CTG GAG TGC CCC GGC GGT CGC CAC CTG ACC TGC CAC CTG CAC
 M   A   L   E   C   P   G   G   R   H   L   T   C   H   L   H

ACC ACC TAC CGC TCC AAG AAG CCC GCC TCC GCC CTG AAG ATG CCC GGC
 T   T   Y   R   S   K   K   P   A   S   A   L   K   M   P   G

TTC CAC TTC GAG GAC CAC CGC ATC GAG ATC CTG GAG GAG GTG GAG AAG
 F   H   F   E   D   H   R   I   E   I   L   E   E   V   E   K

GGC AAG TGC TAC AAG CAG TAC GAG GCC GCC GTG GGC CGC TAC TGC GAC
 G   K   C   Y   K   Q   Y   E   A   A   V   G   R   Y   C   D

GCC GCC CCC TCC AAG CTG GGC CAC AAC
 A   A   P   S   K   L   G   H   N
```

(SEQ ID NO: 9 & 10)

Figure 7. Comparison of various β-actin fusion constructs expressed in L929 fibroblasts.

| FPs fused to β-actin | EGFP | HcRed2A | HcRed2A-tandem | DsRed2 | DsRed2-tandem | M355NA | M355NA-tandem | HcRed | HcRed-tandem |
|---|---|---|---|---|---|---|---|---|---|
| Formation of aggregates | Very Low | Medium | Very low | High | Medium | High | Medium | High | Low |
| Labeling of actin structures | High | Medium | High | Very low | Medium | Very Low | High | Low | High |
| Cytoplasmic background | Low | Medium | Low | High | Low | High | Low | High | Low |
| Total overlay with EGFP | - | Medium | Very high | Very low | Medium | Very low | High | Low | High |

NUCLEIC ACIDS ENCODING LINKED CHROMO/FLUORESCENT DOMAINS AND METHODS FOR USING THE SAME

CROSS-REFERENCE TO RELATED APPLICATIONS

This application is a continuation in part of International Application Serial No. PCT/US02/32560 filed on Oct. 10, 2002 and designating the United States; which application is a continuation-in-part of application Ser. No. 09/976,673 filed on Oct. 12, 2001; and which application (pursuant to 35 U.S.C. § 119 (e)) claims priority to the filing date of U.S. Provisional Patent Application Ser. Nos. 60/356,225 filed Feb. 11, 2002 and 60/383,336 filed May 22, 2002; the disclosures of which are herein incorporated by reference.

INTRODUCTION

1. Field of the Invention

The field of this invention is chromoproteins and fluorescent proteins.

2. Background of the Invention

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc. However, there is continued interest in the development of new labels. Of particular interest is the development of new protein labels, including chromo- and/or fluorescent protein labels.

An important new class of fluorescent proteins that have recently been developed are the Reef Coral Fluorescent Proteins, as described in Matz, M. V., et al. (1999) Nature Biotechnol., 17:969–973. While these fluorescent proteins exhibit many positive attributes, certain versions are prone to unpredictable oligomerization, which can pose problems and consequently limit their applicability.

As such, there is intense interest in the development of versions of this important new class of fluorescent proteins in which the oligomerization properties are predictable. The present invention satisfies this need.

Relevant Literature

U.S. Patents of interest include: U.S. Pat. Nos. 6,066,476; 6,020,192; 5,985,577; 5,976,796; 5,968,750; 5,968,738; 5,958,713; 5,919,445; 5,874,304; and 5,491,084. International Patent Publications of interest include: WO 00/46233; WO 99/49019; and DE 197 18 640 A. Also of interest are: Anderluh et al., Biochemical and Biophysical Research Communications (1996) 220:437–442; Dove et al., Biological Bulletin (1995) 189:288–297; Fradkov et al., FEBS Lett. (2000) 479(3):127–30; Gurskaya et al., FEBS Lett., (2001) 507(1):16–20; Gurskaya et al., BMC Biochem. (2001) 2:6; Lukyanov, K., et al (2000) J Biol Chemistry 275(34): 25879–25882; Macek et al., Eur. J. Biochem. (1995) 234: 329–335; Martynov et al., J Biol Chem. (2001) 276:21012–6; Matz, M. V., et al. (1999) Nature Biotechnol., 17:969–973; Terskikh et al., Science (2000) 290:1585–8; Tsien, Annual Rev. of Biochemistry (1998) 67:509–544; Tsien, Nat. Biotech. (1999) 17:956–957; Ward et al., J. Biol. Chem. (1979) 254:781–788; Wiedermann et al., Jarhrestagung der Deutschen Gesellschact fur Tropenokologie-gto. Ulm. 17–19, February 1999. Poster P-4.20; Yanushevich et al., FEBS Lett (Jan. 30, 2002)511(1–3):11–4; and Yarbrough et al., Proc Natl Acad Sci U S A (2001) 98:462–7.

SUMMARY OF THE INVENTION

Nucleic acid compositions encoding polypeptide products having at least two linked chromo/fluorescent domains, as well as the proteins encoded by the same, are provided. Also provided are the polypeptides encoded by the subject nucleic acids, as well as antibodies to the subject proteins and transgenic cells and organisms. The subject protein and nucleic acid compositions find use in a variety of different applications, e.g., in the production of labeled fusion proteins that have a precise and predictable signal to fusion partner ratio. Finally, kits for use in such applications, e.g., that include the subject nucleic acid compositions, are provided.

BRIEF DESCRIPTION OF THE FIGURES

FIG. 1 provides the nucleotide and amino acid sequences of the Cr-449-tandem embodiment of the present invention (4-amino acid linker between monomers is in double underline). (SEQ ID NO:01 & 02)

FIG. 2 provides the nucleotide and amino acid sequence of the Cr-449-tandem-actin embodiment of the present invention (4-amino acid linker between Cr-449 monomers is noted in double underline; 4-amino acid linker between second Cr-449 and actin is noted in dashed underline). (SEQ ID NO:03 & 04)

FIG. 3 provides the nucleotide and amino acid sequences of the HcRed-Cr1-tandem embodiment of the present invention (4-amino acid linker between monomers is in double underline). (SEQ ID NO:05 & 06)

FIG. 4 provides the nucleotide and amino acid sequences of the AsRed 35-5 NA-tandem embodiment of the present invention (4-amino acid linker between monomers is in double underline). (SEQ ID NO:07 & 08)

FIG. 5 provides the nucleotide and amino acid sequences of the AsRed 35-5D-tandem embodiment of the present invention (4-amino acid linker between monomers is in double underline). (SEQ ID NO:09 & 10)

FIG. 7. Comparison of various β-actin fusion constructs expressed in L929 fibroblasts.

DEFINITIONS

Figure 6:
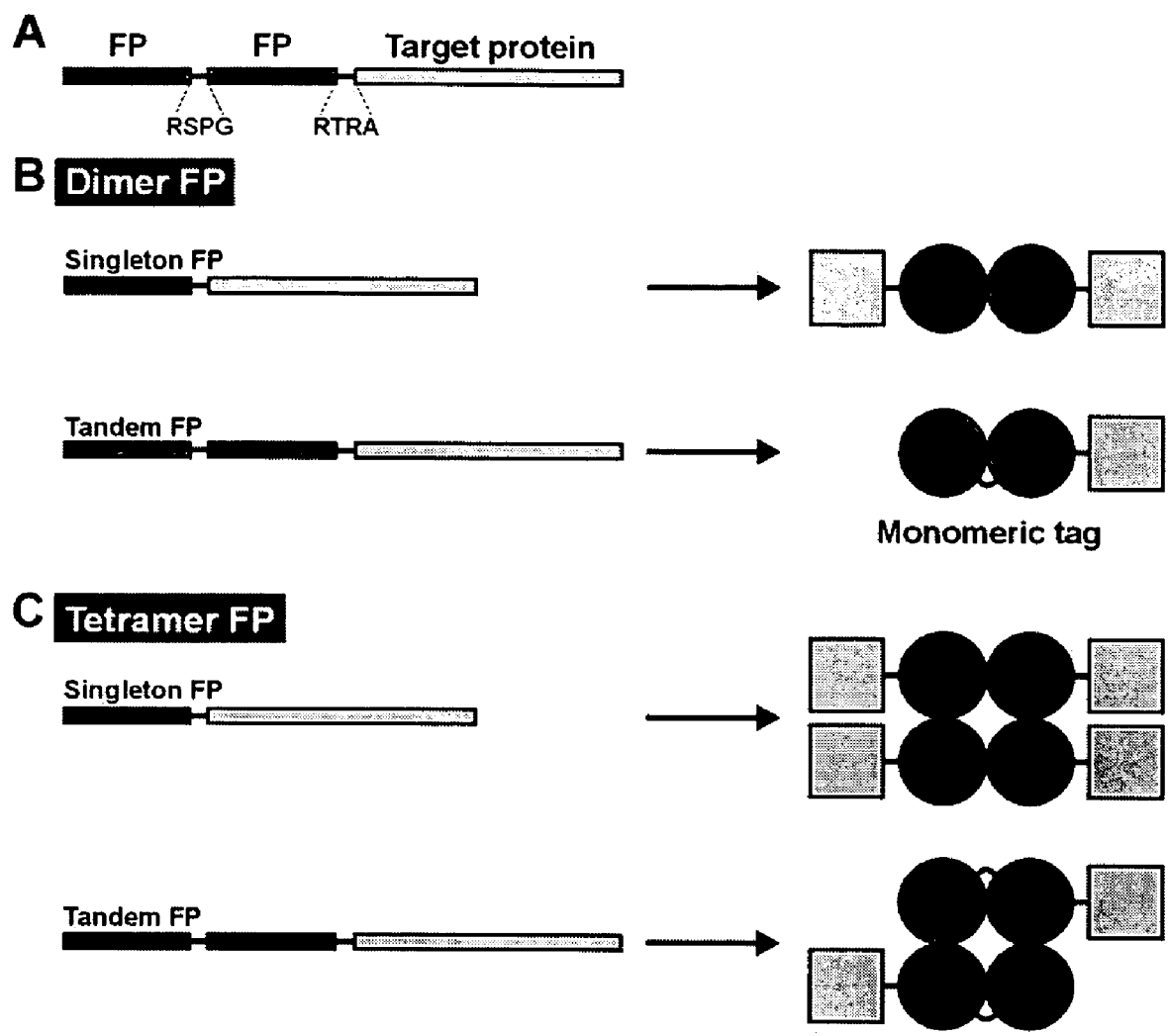
FIGS. 6A to 6C. Schematic representation of the constructs used. (6A) An outline of the coding region of tandem FP fused with target protein. Darker rectangles represent FPs, while the lighter rectangle represents target protein. Short lines correspond to linkers between the first FP, second FP and the target protein. Amino acid sequences of the linkers are shown below: RSPG (SEQ ID NO: 14) and RTRA (SEQ ID NO: 15). (6B) Possible behavior of dimeric FP in fused constructs. Darker circles represent folded FP molecules, while lighter squares indicate folded target protein molecules (other graphical symbols as in 6A). In the case of singleton tags, intermolecular FP dimerization results in forced proximity of two target protein molecules. In contrast, FP in tandem forms an intramolecular dimer and is thus considered a monomeric tag. (6C) Possible behavior of tetrameric FP in fusion constructs. Graphical symbols as in A and B. Intermolecular tetramerization of the singleton tag brings four target molecules into close proximity. In contrast, for tandem tag, each "tetramer" (dimer of dimers) contains only two target proteins.

In accordance with the present invention there may be employed conventional molecular biology, microbiology, and recombinant DNA techniques within the skill of the art.

Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243 (1969), 3552–59 is used.

The term "immunologically active" defines the capability of the natural, recombinant or synthetic chromo/fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651–681. New York: Academic Press.;

Wilson, T. and Hastings, J. W. (1998). Bioluminescence. *Annu Rev Cell Dev Biol* 14, 197–230.). Bioluminescence does not include so-called ultra-weak light emission, which can be detected in virtually all living structures using sensitive luminometric equipment (Murphy, M. E. and Sies, H.(1990). Visible-range low-level chemiluminescence in biological systems. *Meth. Enzymol*.186, 595–610; Radotic, K, Radenovic, C, Jeremic, M. (1998.) Spontaneous ultra-weak bioluminescence in plants: origin, mechanisms and properties. *Gen Physiol Biophys* 17, 289–308), and from weak light emission which most probably does not play any ecological role, such as the glowing of bamboo growth cone (Totsune, H., Nakano, M., Inaba, H.(1993). Chemiluminescence from bamboo shoot cut. *Biochem. Biophys. Res Comm*. 194, 1025–1029) or emission of light during fertilization of animal eggs (Klebanoff, S. J., Froeder, C. A., Eddy, E. M., Shapiro, B. M. (1979). Metabolic similarities between fertilization and phagocytosis. Conservation of peroxidatic mechanism. *J. Exp. Med*. 149, 938–953; Schomer, B. and Epel, D. (1998). Redox changes during fertilization and maturation of marine invertebrate eggs. *Dev Biol* 203, 1–11).

DESCRIPTION OF THE SPECIFIC EMBODIMENTS

Nucleic acid compositions encoding polypeptide products having at least two linked chromo/fluorescent domains, as well as the proteins encoded by the same, are provided. Also provided are the polypeptides encoded by the subject nucleic acids, as well as antibodies to the subject proteins and transgenic cells and organisms. The subject protein and nucleic acid compositions find use in a variety of different applications, e.g., in the production of labeled fusion proteins that have a precise and predictable signal to fusion partner ratio. Finally, kits for use in such applications, e.g., that include the subject nucleic acid compositions, are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, methodologies and other invention components that are described in the publications which might be used in connection with the presently described invention.

In further describing the subject invention, the subject nucleic acid compositions will be described first, followed by a discussion of the subject protein compositions, antibody compositions and transgenic cells/organisms. Next a review of representative methods in which the subject proteins find use is provided.

Nucleic Acid Compositions

As summarized above, the subject invention provides nucleic acid compositions encoding polypeptide products that include at least two chromo/fluorescent domains, where the two or more chromo/fluorescent domains may or may not be linked by a linking domain, i.e., the two or more domains are optionally linked by a linking domain. The two or more chromo/fluorescent domains are located in "head-to-tail" fashion, such that the domains are in tandem. A feature of many embodiments of the subject nucleic acids is that the two or more chromo/fluorescent domains of the encoded polypeptides associate with each other, at least under intracellular conditions, so that the encoded polypeptide assumes a tertiary structure which is the product of the two or more chromo/fluorescent domains associating-with each other. In other words, the two or more chromo/fluorescent domains "oligomerize" with each other to produce a polypeptide having a "linked" oligomeric "tertiary" structure. For example, where the encoded polypeptide has two chromo/fluorescent domains, these domains associate with each other in the encoded product to produce a "linked" dimeric structure.

The number of distinct chromo/fluorescent domains in the encoded polypeptides may vary and is at least 2, where the number may be as high as 10 or higher, but typically does not exceed about 8, usually does not exceed about 6 and more usually does not exceed about 4, where in certain embodiments, the number of distinct chromo/fluorescent domains in the encoded polypeptides is 2, 3, or 4, and in many embodiments is 2 or 3 and often is 2. The chromo/fluorescent domains are described in greater detail below.

As mentioned above, in the encoded polypeptides the two or more chromo/fluorescent domains may or may not be linked by a linking domain, i.e., the two or more chromo/fluorescent domains are optionally joined by a linking domain. The linking domain often ranges from about 1 to about 50 residues in length, where in many embodiments, the linking domain is from about 1 to about 25 residues in length, usually from about 1 to about 15 residues in length and more usually from about 1 to about 10 residues in length, and in certain preferred embodiments is from about 1 to about 5 residues in length. The linking domain may have any convenient residue sequence, i.e., amino acid sequence, where the domain may be a flexible domain or assume a rigid configuration, as desired.

As mentioned above, the encoded polypeptides include two or more chromo/fluorescent domains. By chromo and/or fluorescent domain is meant a domain that is colored, i.e., is pigmented, where the domain may or may not be fluorescent, e.g., it may exhibit low, medium or high fluorescence upon irradiation with light of an excitation wavelength. In any event, the chromo/fluorescent domains are those in which the colored characteristic, i.e., the chromo and/or fluorescent characteristic, is one that arises from the interaction of two or more residues of the domain, and not from a single residue, more specifically a single side chain of a single residue, of the protein. As such, chromo/fluorescent domains of the subject invention do not include domains that exhibit fluorescence only from residues that act by themselves as intrinsic fluors, i.e., tryptophan, tyrosine and phenylalanine. As such, the chromo/fluorescent domains of the subject invention are domains whose fluorescence arises from some structure in the domain that is other than the above specified single residues, e.g., it arises from an interaction of two or more residues.

In many embodiments, the chromo/fluorescent domains of the polypeptides encoded by the subject nucleic acids are wild type proteins (or mutants thereof) that occur in *Cnidarian* species, e.g., *Anthozoan* species. In certain embodiments, the chromo/fluorescent domains are wild type proteins (or mutants thereof that are either from: (1) non-bioluminescent species, often non-bioluminescent *Cnidarian* species, e.g., non-bioluminescent *Anthozoan* species; or (2) from *Anthozoan* species that are not *Pennatulacean* species, i.e., that are not sea pens. As such, the chromo/fluorescent domains are proteins (or mutants thereof) from bioluminescent *Anthozoan* species, so long as these species are not *Pennatulacean* species, e.g., that are not *Renillan* or *Ptilosarcan* species. Of particular interest in certain embodiments are chromo/fluorescent domains that are the following wild type proteins (or mutants thereof): (1) amFP485, cFP484, zFP506, zFP540, drFP585, dsFP484, asFP600, dgFP512, dmFP592, as disclosed in application Ser. No. 10/006,922, the disclosure of which is herein incorporated by reference; (2) hcFP640, as disclosed in application Ser. No. 09/976,673, the disclosure of which is herein incorporated by reference; (3) CgCP, as disclosed in application Ser. No. 60/255,533, the disclosure of which is herein incorporated by reference; and (4) hcriGFP, zoanRFP, scubGFP1, scubGFP2, rfloRFP, rfloGFP, mcavRFP, mcavGFP, cgigGFP, afraGFP, rfloGFP2, mcavGFP2, mannFP, as disclosed in application Ser. No. 60/332,980, the disclosure of which is herein incorporated by reference.

Nucleic acids encoding mutants of the above specific wild type proteins are also of interest for use as chomo/fluorescent domains of the encoded polypeptides. Mutant nucleic acids can be generated by random mutagenesis or targeted mutagenesis, using well-known techniques which are routine in the art. In some embodiments, chromo- or fluorescent domains encoded by nucleic acids encoding homologues or mutants have the same fluorescent properties as the parent wild-type fluorescent protein. In other embodiments, homologue or mutant nucleic acids encode chromo- or fluorescent proteins with altered spectral properties, as compared to the parent.

One category of mutant that is of particular interest is the non-aggregating mutant. In many embodiments, the non-aggregating mutant differs from the parent wild type sequence by a mutation in the N-terminus that modulates the charges appearing on side groups of the N-terminus residues, e.g., to reverse or neutralize the charge, in a manner sufficient to produce a non-aggregating mutant of the naturally occurring protein or mutant, where a particular protein is considered to be non-aggregating if it is determined be non-aggregating using the assay reported in U.S. patent application Ser. No. 60/270,983, the disclosure of which is herein incorporated by reference. More specifically, basic residues located near the N-termini of the proteins are substituted, e.g., Lys and Arg residues close to the N-terminus are substituted with negatively charged or neutral residues. Specific non-aggregating mutants of interest include, but are not limited to: FP1-NA; FP3-NA; FP4-NA; FP6-NA; E5-NA; 6/9Q-NA; 7A-NA; and the like, where these particular non-aggregating mutants are further described in application Ser. No. 10/006,922 filed Dec. 4, 2001, the disclosure of which is herein incorporated by reference.

Another category of mutant of particular interest is the modulated oligomerization mutant. A mutant is considered to be a modulated oligomerization mutant if its oligomerization properties are different as compared to the wild type protein. For example, if a particular mutant oligomerizes to a greater or lesser extent than the wild type, it is considered to be an oligomerization mutant. Of particular interest are oligomerization mutants that do not oligomerize, i.e., are monomers under physiological (e.g., intracellular) conditions, or oligomerize to a lesser extent that the wild type, e.g., are dimers or trimers under intracellular conditions. For example, in certain embodiments, the chromo/fluorescent domains are proteins that naturally for tetramers. In other other embodiments, the domains are mutants of tetrameric forming proteins, where the mutants form dimers but not tetramers.

By nucleic acid composition is meant a composition comprising a sequence of DNA having an open reading frame that encodes a polypeptide of the subject invention, as described above, and is capable, under appropriate conditions, of being expressed as a polypeptide of the subject invention, as described above. Also encompassed in this term are nucleic acids that are homologous, substantially similar or identical to the nucleic acids of the present invention. Thus, the subject invention provides coding sequences encoding the polypeptides of the subject invention, as well as homologues thereof.

In addition to the above-described specific nucleic acid compositions, also of interest are homologues of the above sequences. In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). Of particular interest in certain embodiments are nucleic acids of substantially the same length as the nucleic acid identified as SEQ ID NOS: 1 & 3, where by substantially the same length is meant that any difference in length does not exceed about 20 number %, usually does not exceed about 10 number % and more usually does not exceed about 5 number %; and have sequence identity to any of these sequences of at least about 90%, usually at least about 95% and more usually at least about 99% over the entire length of the nucleic acid. In many embodiments, the nucleic acids have a sequence that is substantially similar (i.e. the same as) or identical to the sequences of SEQ ID NOS: 1 & 3. By substantially similar is meant that sequence identity will generally be at least about 60%, usually at least about 75% and often at least about 80, 85, 90, or even 95%.

Also provided are nucleic acids that encode the proteins encoded by the above described nucleic acids, but differ in sequence from the above described nucleic acids due to the degeneracy of the genetic code.

Also provided are nucleic acids that hybridize to the above-described nucleic acids under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Nucleic acids encoding mutants of the polypeptides of the invention are also provided. Mutant nucleic acids can be generated by random mutagenesis or targeted mutagenesis, using well-known techniques which are routine in the art. In some embodiments, polypeptides encoded by nucleic acids encoding homologues or mutants have the same fluorescent properties as parent polypeptide. In other embodiments, homologue or mutant nucleic acids encode polypeptides with altered spectral properties.

The subject nucleic acids may be present in an appropriate vector for extrachromosomal maintenance or for integration into a host genome, as described in greater detail below.

The nucleic acid compositions of the subject invention may encode all or a part of the subject polypeptides. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least about 15 nt, usually at least about 18 nt or about 25 nt, and may be at least about 50 nt. In some embodiments, the subject nucleic acid molecules may be about 100 nt, about 200 nt, about 300 nt, about 400 nt, about 500 nt, about 600 nt, about 700 nt, or about 720 nt in length. The subject nucleic acids may encode fragments of the subject proteins or the full-length proteins, e.g., the subject nucleic acids may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein.

The subject polynucleotides and constructs thereof are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual*, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Also provided are nucleic acids that encode fusion proteins containing the two or more chromo/fluorescent domains, or fragments thereof, in tandem, which are fused to a second protein, e.g., a degradation sequence, a signal peptide, a protein of interest (i.e., a protein being studied), etc. Fusion proteins may comprise a subject polypeptide, or fragment thereof, and a fusion partner fused in-frame at the N-terminus and/or C-terminus of the subject polypeptide (that includes two or more, often two, chromo/fluorescent domains linked by a linking group, as described above). Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the chromo/fluorescent domains of the fusion protein, and in certain embodiments is not a Cnidarian protein or derivative/fragment thereof, i.e., it is not found in *Cnidarian* species. An important feature of such fusion proteins is that, under intracellular conditions, each fusion partner protein is associated with a known number of chromo/fluorescent domains, such that fusion proteins having a predictable signal to fusion partner ratio are produced. In the preferred embodiments having two chromo/fluorescent domains arranged in tandem and linked by a linking group, the two chorom/fluorescent domains associate with each other to produce a dimeric structure fused to a fusion partner, which structure does not associate with any additional chromo/fluorescent domains, such that a fusion protein is produced which is known to have two chromo/fluorescent domains for the fusion partner. Of particular interest in these embodiments is two tandem chromo/fluorescent domains that associated together to produce a linked dimer that behaves like a monomer, i.e., the dimeric structure does not oligimerize with one or more additional chromo/fluorescent domains/proteins.

Also provided are constructs comprising the subject nucleic acids inserted into a vector, where such constructs may be used for a number of different applications, including propagation, protein production, etc. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject polypeptides. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, Xenopus Oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res*. (1980) 8:4057; EP 0 036,776; U.S. Pat. No. 4,551,433; DeBoer et al., *Proc. Natl. Acad. Sci. (USA)* (1983) 80:21–25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol*. (1983) 153:163; Kurtz et al., *Mol. Cell. Biol*. (1986) 6:142; Kunze et al., *J. Basic Microbiol*. (1985) 25:141; Gleeson et al., *J. Gen. Microbiol*. (1986) 132:3459; Roggenkamp et al., *Mol. Gen. Genet*. (1986) 202:302; Das et al., *J. Bacteriol*. (1984) 158:1165; De Louvencourt et al., *J. Bacteriol*. (1983) 154: 737; Van den Berg et al., *Bio/Technology* (1990) 8:135; Kunze et al., *J. Basic Microbiol*. (1985) 25:141; Cregg et al., *Mol. Cell. Biol*. (1985) 5:3376; U.S. Pat. Nos. 4,837,148 and 4,929,555; Beach and Nurse, *Nature* (1981) 300:706; Davidow et al., *Curr. Genet*. (1985) 10:380; Gaillardin et al., *Curr. Gene*t. (1985) 10:49; Ballance et al., *Biochem. Biophys. Res. Commun*. (1983) 112:284–289; Tilburn et al., *Gene* (1983) 26:205–221; Yelton et al., *Proc. Natl. Acad. Sci. (USA)* (1984) 81:1470–1474; Kelly and Hynes, *EMBO J*. (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol*. (1988) 69:765–776; Miller et al., *Ann. Rev. Microbiol*. (1988) 42:177; Carbonell et al., *Gene* (1988) 73:409; Maeda et al., *Nature* (1985) 315:592–594; Lebacq-Verheyden et al., *Mol. Cell. Biol*. (1988) 8:3129; Smith et al., *Proc. Natl. Acad. Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J*. (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz*. (1979) 58:44, Barnes and Sato, *Anal. Biochem*. (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

The subject nucleic acids may be mutated in various ways known in the art to generate targeted changes in the sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet*. 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), Biotechniques 13:592–6; Jones and Winistorfer (1992), Biotechniques 12:528–30; Barton et al. (1990), Nucleic Acids Res 18:7349–55; Marotti and Tomich (1989), Gene Anal. Tech. 6:67–70; and Zhu (1989), Anal Biochem 177:120–4. Such mutated nucleic acid derivatives may be used to study structure-function relationships of a particular chromo/fluorescent protein, or to alter properties of the protein that affect its function or regulation.

Also of interest are humanized versions of the subject nucleic acids. As used herein, the term "humanized" refers to changes made to the nucleic acid sequence to optimize the codons for expression of the protein in human cells (Yang et al., Nucleic Acids Research 24 (1996), 4592–4593). See also U.S. Pat. No. 5,795,737 which describes humanization of proteins, the disclosure of which is herein incorporated by reference.

Protein/Polypeptide Compositions

Also provided by the subject invention are polypeptides encoded by the subject nucleic acids, as well as polypeptide compositions related thereto. The term polypeptide composition as used herein refers to both the full-length protein, as well as portions or fragments thereof. Also included in this term are variations of the parental polypeptide, where such variations are homologous or substantially similar to the parental polypeptide, and mutants of the parental polypeptides, as described in greater detail below.

In many embodiments, the chromo/fluorescent domains of the subject polypeptides have an absorbance maximum ranging from about 300 to 700, usually from about 350 to 650 and more usually from about 400 to 600 nm. Where the subject domains are fluorescent domains, by which is meant that they can be excited at one wavelength of light following which they will emit light at another wavelength, the excitation spectra of the subject domains typically ranges from about 300 to 700, usually from about 350 to 650 and more usually from about 400 to 600 nm while the emission spectra of the subject domains typically ranges from about 400 to 800, usually from about 425 to 775 and more usually from about 450 to 750 nm. The subject domains generally have a maximum extinction coefficient that ranges from about 10,000 to 50,000 and usually from about 15,000 to 45,000. The subject domains typically range in length from about 150 to 300 and usually from about 200 to 300 amino acid residues, and generally have a molecular weight ranging from about 15 to 35 kDa, usually from about 17.5 to 32.5 kDa.

In certain embodiments, the subject domains are bright, where by bright is meant that the chromoproteins and their fluorescent mutants can be detected by common methods (e.g., visual screening, spectrophotometry, spectrofluorometry, fluorescence microscopy, by FACS machines, etc.) Fluorescence brightness of particular fluorescent proteins is determined by its quantum yield multiplied by maximal extinction coefficient. Brightness of a chromoproteins may be expressed by its maximal extinction coefficient.

In certain embodiments, the subject domains fold rapidly following expression in the host cell. By rapidly folding is meant that the domains achieve their tertiary structure that gives rise to their chromo- or fluorescent quality in a short period of time. In these embodiments, the domains fold in a period of time that generally does not exceed about 3 days, usually does not exceed about 2 days and more usually does not exceed about 1 day.

Specific domains of interest are polypeptides or variants of chromo/fluoroproteins (and mutants thereof) from the following specific Anthozoan species: Anemonia majano, Clavularia sp., Zoanthus sp., Zoanthus sp., Discosoma striata, Discosoma sp. "red", Anemonia sulcata, Discosoma sp "green", Discosoma sp."magenta," as well as the additional specific species listed above.

Homologs or proteins (or fragments thereof that vary in sequence from the amino acid sequences of the above provided specific polypeptides are also of interest as chromo/fluorescent domains. By homolog is meant a protein having at least about 10%, usually at least about 20% and more usually at least about 30%, and in many embodiments at least about 35%, usually at least about 40% and more usually at least about 60% amino acid sequence identity to the protein of the subject invention, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5:151–153. (Parameters used are ktuple 1, gap penalty 3, window, 5 and diagonals saved 5). In many embodiments, homologues of interest have much higher sequence identify, e.g., 65%, 70%, 75%, 80%, 85%, 90% or higher.

Also provided are domains that are substantially identical to the sequences of the above provided specific proteins, where by substantially identical is meant that the protein has an amino acid sequence identity to the one of the above specifically provided proteins of at least about 60%, usually at least about 65% and more usually at least about 70%, where in some instances the identity may be much higher, e.g., 75%, 80%, 85%, 90%, 95% or higher.

In many embodiments, the subject homologues have structural features found in the above provided specific sequences, where such structural features include the β-can fold.

Proteins which are mutants of the above specifically described proteins are also of interest as chromo/fluorescent domains. Mutants may retain biological properties of the wild-type (e.g., naturally occurring) proteins, or may have biological properties which differ from the wild-type proteins. The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from A. Victoria), and the like; in vivo and/or in vitro stability (e.g., half-life); etc. Mutants include single amino acid changes, deletions of one or more amino acids, N-terminal truncations, C-terminal truncations, insertions, etc.

Mutants can be generated using standard techniques of molecular biology, e.g., random mutagenesis, and targeted mutagenesis. Several mutants are described herein. Given the guidance provided in the Examples, and using standard techniques, those skilled in the art can readily generate a wide variety of additional mutants and test whether a biological property has been altered. For example, fluorescence intensity can be measured using a spectrophotometer at various excitation wavelengths.

Mutants of the above specifically provided proteins are also provided. Generally such polypeptides include an amino acid sequence encoded by an open reading frame (ORF) of the gene encoding the subject wild type protein, including the full length protein and fragments thereof, particularly biologically active fragments and/or fragments corresponding to functional domains, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length. In some embodiments, the subject polypeptides are about 25 aa, about 50 aa, about 75 aa, about 100 aa, about 125 aa, about 150 aa, about 200 aa, about 210 aa, about 220 aa, about 230 aa, or about 240 aa in length, up to the entire protein. In some embodiments, a protein fragment retains all or substantially all of a biological property of the wild-type protein.

The subject proteins and polypeptides that make up the chomo/fluorescent domains may be synthetically produced using any convenient protocol, e.g., by expressing a recombinant gene or nucleic acid coding sequence encoding the protein of interest in a suitable host, as described above. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Antibody Compositions

Also provided are antibodies that specifically bind to the subject encoded polypeptides. Suitable antibodies are obtained by immunizing a host animal with peptides comprising all or a portion of the subject polypeptides. Suitable host animals include mouse, rat sheep, goat, hamster, rabbit, etc. The immunogen may comprise the complete protein, or fragments and derivatives thereof.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) $J.B.C.$ 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) $P.N.A.S.$ 84:3439 and (1987) $J. Immunol.$ 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Transgenics

The subject nucleic acids can be used to generate transgenic, non-human plants or animals or site specific gene modifications in cell lines. Transgenic cells of the subject invention include one or more nucleic acids according to the subject invention present as a transgene, where included within this definition are the parent cells transformed to include the transgene and the progeny thereof. In many embodiments, the transgenic cells are cells that do not normally harbor or contain a nucleic acid according to the subject invention. In those embodiments where the transgenic cells do naturally contain the subject nucleic acids, the nucleic acid will be present in the cell in a position other than its natural location, i.e. integrated into the genomic material of the cell at a non-natural location. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of the endogenous gene is at least reduced if not eliminated. Transgenic organisms of interest also include cells and multicellular organisms, e.g., plants and animals, in which the protein or variants thereof is expressed in cells or tissues where it is not normally expressed and/or at levels not normally present in such cells or tissues.

DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275–295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is *Agrobacterium* mediated transformation. With *Agrobacterium* mediated transformation, co-integrative or binary vectors comprising the exogenous DNA are prepared and then introduced into an appropriate *Agrobacterium* strain, e.g. *A. tumefaciens*. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

UTILITY

The subject polypeptides find use in a variety of different applications, where the applications necessarily differ depending on whether the chromo/fluorescent domains are chromoproteins or fluorescent proteins. Representative uses for each of these types of proteins will be described below, where the following described uses are merely representative and are in no way meant to limit the use of the subject proteins to those described below.

Chromoproteins

The subject chromoprotein containing polypeptides of the present invention find use in a variety of different applications. One application of interest is the use of the subject proteins as coloring agents which are capable of imparting color or pigment to a particular composition of matter. Of particular interest in certain embodiments are non-toxic chromoproteins. The subject chromoproteins may be incorporated into a variety of different compositions of matter, where representative compositions of matter include: food compositions, pharmaceuticals, cosmetics, living organisms, e.g., animals and plants, and the like. Where used as a coloring agent or pigment, a sufficient amount of the chromoprotein is incorporated into the composition of matter to impart the desired color or pigment thereto. The chromoprotein may be incorporated into the composition of matter using any convenient protocol, where the particular protocol employed will necessarily depend, at least in part, on the nature of the composition of matter to be colored. Protocols that may be employed include, but are not limited to: blending, diffusion, friction, spraying, injection, tattooing, and the like.

The chromoproteins may also find use as labels in analyte detection assays, e.g., assays for biological analytes of interest. For example, the chromoproteins may be incorporated into adducts with analyte specific antibodies or binding fragments thereof and subsequently employed in immunoassays for analytes of interest in a complex sample, as described in U.S. Pat. No. 4,302,536; the disclosure of which is herein incorporated by reference. Instead of antibodies or binding fragments thereof, the subject chromoproteins or chromogenic fragments thereof may be conjugated to ligands that specifically bind to an analyte of interest, or other moieties, growth factors, hormones, and the like; as is readily apparent to those of skill in the art.

In yet other embodiments, the subject chromoproteins may be used as selectable markers in recombinant DNA applications, e.g., the production of transgenic cells and organisms, as described above. As such, one can engineer a particular transgenic production protocol to employ expression of the subject chromoproteins as a selectable marker, either for a successful or unsuccessful protocol. Thus, appearance of the color of the subject chromoprotein in the phenotype of the transgenic organism produced by a particular process can be used to indicate that the particular organism successfully harbors the transgene of interest, often integrated in a manner that provides for expression of the transgene in the organism. When used a selectable marker, a nucleic acid encoding for the subject chromoprotein can be employed in the transgenic generation process, where this process is described in greater detail supra. Particular transgenic organisms of interest where the subject proteins may be employed as selectable markers include transgenic plants, animals, bacteria, fungi, and the like.

In yet other embodiments, the chromoproteins (and fluorescent proteins) of the subject invention find use in sunscreens, as selective filters, etc., in a manner similar to the uses of the proteins described in WO 00/46233.

Fluorescent Proteins

The subject fluorescent protein containing polypeptides of the present invention (as well as other components of the subject invention described above) find use in a variety of different applications, where such applications include, but are not limited to, the following. The first application of interest is the use of the subject proteins in fluorescence resonance energy transfer (FRET) applications. In these applications, the subject proteins serve as donor and/or acceptors in combination with a second fluorescent protein or dye, e.g., a fluorescent protein as described in Matz et al., Nature Biotechnology (October 1999) 17:969–973, a green fluorescent protein from *Aequoria victoria* or fluorescent mutant thereof, e.g., as described in U.S. Pat. Nos. 6,066, 476; 6,020,192; 5,985,577; 5,976,796; 5,968,750; 5,968, 738; 5,958,713; 5,919,445; 5,874,304, the disclosures of which are herein incorporated by reference, other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418, 155; 5,330,906; 5,229,285; 5,221,623; 5,182,202; the disclosures of which are herein incorporated by reference. Specific examples of where FRET assays employing the subject fluorescent proteins may be used include, but are not limited to: the detection of protein-protein interactions, e.g., mammalian two-hybrid system, transcription factor dimerization, membrane protein multimerization, multiprotein complex formation, etc., as a biosensor for a number of different events, where a peptide or protein covalently links a FRET fluorescent combination including the subject fluorescent proteins and the linking peptide or protein is, e.g., a protease specific substrate, e.g., for caspase mediated cleavage, a linker that undergoes conformational change upon receiving a signal which increases or decreases FRET, e.g., PKA regulatory domain (cAMP-sensor), phosphorylation, e.g., where there is a phosphorylation site in the linker or the linker has binding specificity to phosphorylated/dephosphorylated domain of another protein, or the linker has $Ca^{2+}$ binding domain. Representative fluorescence resonance energy transfer or FRET applications in which the subject proteins find use include, but are not limited to, those described in: U.S. Pat. Nos. 6,008,373; 5,998,146; 5,981, 200; 5,945,526; 5,945,283; 5,911,952; 5,869,255; 5,866, 336; 5,863,727; 5,728,528; 5,707,804; 5,688,648; 5,439, 797; the disclosures of which are herein incorporated by reference.

Another application in which the subject fluorescent proteins find use is BRET (Bioluminescence Resonance Energy Transfer). BRET is a protein-protein interaction assay based on energy transfer from a bioluminescent donor to a fluorescent acceptor protein. The BRET signal is measured by the amount of light emitted by the acceptor to the amount of light emitted by the donor. The ratio of these two values increases as the two proteins are brought into proximity. The BRET assay has been amply described in the literature. See, e.g., U.S. Pat. Nos. 6,020,192; 5,968,750; and 5,874,304; and Xu et al. (1999) *Proc. Natl. Acad. Sci.* USA 96:151–156. BRET assays may be performed by genetically fusing a bioluminescent donor protein and a fluorescent acceptor protein independently to two different biological partners to make partner A-bioluminescent donor and partner B-fluorescent acceptor fusions. Changes in the interaction between the partner portions of the fusion proteins, modulated, e.g., by ligands or test compounds, can be monitored by a change in the ratio of light emitted by the bioluminescent and fluorescent portions of the fusion proteins. In this application, the subject proteins serve as donor and/or acceptor proteins. BRET assays can be used in many of the assays as FRET, which assays are noted above.

The subject fluorescent proteins also find use as biosensors in prokaryotic and eukaryotic cells, e.g. as $Ca^{2+}$ ion indicator; as pH indicator, as phorphorylation indicator, as an indicator of other ions, e.g., magnesium, sodium, potassium, chloride and halides. For example, for detection of Ca ion, proteins containing an EF-hand motif are known to translocate from the cytosol to membranes upon $Ca^{2+}$ binding. These proteins contain a myristoyl group that is buried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such a EF-hand containing protein to Fluorescent Proteins (FP) could make it an indicator of intracellular $Ca^{2+}$ by monitoring the translocation from the cytosol to the plasma membrane by confocal microscopy. EF-hand proteins suitable for use in this system include, but are not limited to: recoverin (1–3), calcineurin B, troponin C, visinin, neurocalcin, calmodulin, parvalbumin, and the like. For pH, a system based on hisactophilins may be employed. Hisactophilins are myristoylated histidine-rich proteins known to exist in *Dictyostelium*. Their binding to actin and acidic lipids is sharply pH-dependent within the range of cytoplasmic pH variations. In living cells membrane binding seems to override the interaction of hisactophilins with actin filaments. At $pH \leq 6.5$ they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing FPs (Fluoresent Proteins) to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1–2 min and reaches a steady state level after 5–10 min. The reverse reaction takes place on a similar time scale. As such, hisactophilin-fluorescent protein fusion protein that acts in an analogous fashion can be used to monitor cytosolic pH changes in real time in live mammalian cells. Such methods have use in high throuhgput applications, e.g., in the measurement of pH changes as consequence of growth factor receptor activation (e.g. epithelial or platelet-derived growth factor) chemotactic stimulation/cell locomotion, in the detection of intracellular pH changes as second messenger, in the monitoring of intracellular pH in pH manipulating experiments, and the like. For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention makes the above a detector system for PKC activity. When phosphorylated by PKC, the fusion protein translocates from the plasma membrane to the cytosol. This translocation is followed by standard fluorescence microscopy or confocal microscopy e.g. using the Cellomics technology or other High Content Screening systems (e.g. Universal Imaging Corp./Becton Dickinson). The above reporter system has application in High Content Screening, e.g., screening for PKC inhibitors, and as an indicator for PKC activity in many screening scenarios for potential reagents interfering with this signal transduction pathway. Methods of using fluorescent proteins as biosensors also include those described in U.S. Pat. Nos. 972,638; 5,824,485 and 5,650,135 (as well as the references cited therein) the disclosures of which are herein incorporated by reference.

The subject fluorescent proteins also find use in applications involving the automated screening of arrays of cells expressing fluorescent reporting groups by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, etc.; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin) as tools for High Content Screening: co-localization of other fluorescent fusion proteins with these localization markers as indicators of movements of intracellular fluorescent fusion proteins/peptides or as marker alone; and the like. Examples of applications involving the automated screening of arrays of cells in which the subject fluorescent proteins find use include: U.S. Pat. No. 5,989,835; as well as WO/0017624; WO 00/26408; WO 00/17643; and WO 00/03246; the disclosures of which are herein incorporated by reference.

The subject fluorescent proteins also find use in high through-put screening assays. The subject fluorescent proteins are stable proteins with half-lives of more than 24 h. Also provided are destabilized versions of the subject fluorescent proteins with shorter half-lives that can be used as transcription reporters for drug discovery. For example, a protein according to the subject invention can be fused with a putative proteolytic signal sequence derived from a protein with shorter half-life, e.g., PEST sequence from the mouse ornithine decarboxylase gene, mouse cyclin B1 destruction box and ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening, e.g., AP1, NFAT, NFkB, Smad, STAT, p53, E2F, Rb, myc, CRE, ER, GR and TRE, and the like.

The subject proteins can be used as second messenger detectors, e.g., by fusing the subject proteins to specific domains: e.g., PKCgamma Ca binding domain, PKCgamma DAG binding domain, SH2 domain and SH3 domain, etc.

Secreted forms of the subject proteins can be prepared, e.g. by fusing secreted leading sequences to the subject proteins to construct secreted forms of the subject proteins, which in turn can be used in a variety of different applications.

The subject proteins also find use in fluorescence activated cell sorting applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo marker in animals (e.g., transgenic animals). For example, expression of the subject protein can be driven by tissue specific promoters, where such methods find use in research for gene therapy, e.g., testing efficiency of transgenic expression, among other applications. A representative application of fluorescent proteins in transgenic animals that illustrates this class of applications of the subject proteins is found in WO 00/02997, the disclosure of which is herein incorporated by reference.

Additional applications of the subject proteins include: as markers following injection into cells or animals and in calibration for quantitative measurements (fluorescence and protein); as markers or reporters in oxygen biosensor devices for monitoring cell viability; as markers or labels for animals, pets, toys, food, etc.; and the like.

The subject fluorescent proteins also find use in protease cleavage assays. For example, cleavage inactivated fluorescence assays can be developed using the subject proteins, where the subject proteins are engineered to include a protease specific cleavage sequence without destroying the fluorescent character of the protein. Upon cleavage of the fluorescent protein by an activated protease fluorescence would sharply decrease due to the destruction of a functional chromophor. Alternatively, cleavage activated fluorescence can be developed using the subject proteins, where the subject proteins are engineered to contain an additional spacer sequence in close proximity/or inside the chromophor. This variant would be significantly decreased in its fluorescent activity, because parts of the functional chromophor would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application could be developed in assays for a variety of different types of proteases, e.g., caspases, etc.

The subject proteins can also be used is assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes also allowing colocalization of membrane proteins in specific phospholipid rafts can be accomplished with the subject proteins. For example, the PH domain of GRP1 has a high affinity to phosphatidylinositol tri-phosphate (PIP3) but not to PIP2. As such, a fusion protein between the PH domain of GRP1 and the subject proteins can be constructed to specifically label PIP3 rich areas in biological membranes.

Yet another application of the subject proteins is as a fluorescent timer, in which the switch of one fluorescent color to another (e.g. green to red) concomitant with the ageing of the fluorescent protein is used to determine the activation/deactivation of gene expression, e.g., developmental gene expression, cell cycle dependent gene expression, circadian rhythm specific gene expression, and the like.

The subject fluorescent proteins of the subject invention may also be used in cell labeling applications, as described in U.S. application Ser. No. 60/261,448; the disclosure of which is herein incorporated by reference.

The antibodies of the subject invention, described above, also find use in a number of applications, including the differentiation of the subject proteins from other fluorescent proteins.

Kits

Also provided by the subject invention are kits for use in practicing one or more of the above described applications, where the subject kits typically include elements for making the subject polypeptides, e.g., a construct comprising a vector that includes a coding region for the subject protein. The subject kit components are typically present in a suitable storage medium, e.g., buffered solution, typically in a suitable container. Also present in the subject kits may be antibodies to the provided protein. In certain embodiments, the kit comprises a plurality of different vectors each encoding the subject polypeptides, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Fusion Constructs

A Cr-44-9-tandem (linked dimer), and a Cr-44-9-tandem-actin fusion were constructed. The amino acid sequence and encoding nucleotide sequence for the Cr-44-9 tandem fusion protein are provided in FIG. 1 (SEQ ID NOs: 1 & 2). The amino acid and encoding nucleotide sequence for the Cr-44-9 tandem-actin fusion protein are provided in FIG. 2 (SEQ ID NOs: 3 & 4). The above constructs were expressed in mammalian cells, and the encoded fluorescent proteins were detectable.

The following additional tandem constructs were prepared: HcRed-cr-1 tandem (FIG. 3; SEQ ID NO:5&6); AsRed-35-5NA tandem (FIG. 4; SEQ ID NO:7 & 8); and AsRed-35-5D tandem (FIG. 5; SEQ ID NO:9 & 10). Like the Cr-44-9 tandem construct, good results were obtained when these tandems were fused to actin—the tandems were incorporated into the actin filaments.

II. Additional Constructs and Characterization

A. Materials and Methods

1. Plasmid construction. pEGFP-Actin (Clontech) was used as the parent vector for the construction of all fusion plasmids. HcRed2A, HcRed, M355NA and DsRed2 coding regions were cloned into this vector between AgeI and BglII restriction sites, in lieu of the EGFP-coding region. To create tandems, the second copy of the corresponding FP was cloned into these plasmids (between the first FP and β-actin genes) using the BglII and EcoRV restriction sites. All plasmids contained the four amino acid linker, RTRA, between FP and actin. In the case of tandems, FP genes were separated by the four amino acid linker, RSPG. The fibrillarin coding region was amplified with primers, 5'-GGTG CTCGAGCCATGAAGCCAGGATTCAG (SEQ ID NO:11) and 5'-GGTGGGATCCTCAGTTCTTCACCTTGGGGG (SEQ ID NO:12) (restriction sites are underlined) using Marathon-Ready Human Liver cDNA (Clontech) as a template, and cloned between XhoI and BamHI restriction sites, in lieu of the actin-coding region.

For prokaryotic expression of FP, full-length coding regions were cloned into the pQE30 vector (Qiagen). Proteins fused to an N-terminal 6× His tag were expressed in *E. coli* XL1 Blue strain (Invitrogen) and purified using the TALON metal-affinity resin (Clontech). Gel filtration analyses were performed as described in Gurskaya et al., FEBS Lett. (2001) 507:16–20.

2. Cell culture. L929 and HEK293 cells were obtained from ATCC and cultured in standard Dulbecco's modified MEM medium (Invitrogen) supplemented with 10% FBS (Sigma). Cells grown to 50–70% confluence on 18×18 mm coverslips in 35 mm dishes (Falcon) were transfected with the above plasmids, using LipofectAMINE PLUS (Invitrogen) or FuGENE 6 (Roche) reagents for L929 or HEK293 cells, respectively. After transfection (48 h), cells were washed with Dulbecco's PBS and fixed with 4% paraformaldehyde in PBS for 30 min. For fluorescence microscopy, coverslips were mounted on glass slides using Vectashield mounting medium (Vector Laboratories).

3. Fluorescence microscopy and image analyses. Images of fixed cells were acquired with an ORCA-ER digital camera (Hamamatsu) attached to an Eclipse E800 microscope (Nikon) equipped with Plan Apo 100×/1.40 oil immersion objective, using standard GFP/FITC (excitation, 460–505 nm; emission, 510–560 nm), G-2A (excitation, 510–560; emission, LP 590 nm), and TxRed (excitation, 540–580 nm; emission, 600–660 nm) filter sets for EGFP, M355NA, and HcRed or HcRed2A, respectively. Exposure times of 0.24–4.08 s and high-resolution 1×1 binning mode of the camera were employed. Digital images were deconvoluted, pseudocolored, superimposed in AquaCosmos software (Hamamatsu) and further assembled in Adobe Photoshop.

4. FRET assay. A pQE30-based plasmid encoding a triple fusion HcRed2A-HcRed2A-EYFP was constructed. The EYFP-coding region was amplified from the pEYFP-N1 vector (Clontech). An amino acid linker, RTRAPAGIEGRB (SEQ ID NO:13), between the second HcRed2A and EYFP was introduced by polymerase chain reaction (recognition site for factor Xa is underlined). Purified protein was digested with factor Xa (Promega) in buffer containing 100 mM NaCl, 2 mM $CaCl_2$ and 20 mM Tris-Cl, pH 8.0. Fluorescence spectra (excitation at 490 nm) before and after digestion were measured using a Carry Eclipse Fluorescence Spectrophotometer (Varian). Excitation 460–490 nm, emission LP 510 nm and emission LP 610 nm filters were used with an Olympus SZX12 stereomicroscope to visualize protein samples.

B. Results

The following describes a far-red fluorescent tag that may be generally used for protein labeling. The tag is based on two head-to-tail linked identical HcRed2A fluorescent mutants of the chromoprotein hcCP with 640 nm emission maxima. Since purified HcRed2A forms dimers in solution, we hypothesized that covalently linked copies of this protein form intramolecular dimers, which may be used as a non-oligomerizing tag in vivo.

Initially, we tested the HcRed2A-tandem construct in a prokaryotic expression system. Several amino acid linkers of different lengths and compositions between monomers were examined. The best results in terms of rate and completeness of protein maturation and fluorescence brightness were obtained with a four amino acid linker, RSPG (SEQ ID NO: 14), which was subsequently used in all further constructs. Tandem HcRed2A displayed the same spectral characteristics as the parent protein. Moreover, *E. coli* colonies expressing HcRed2A-tandem possessed brighter fluorescence and more rich purple coloration in comparison to colonies with singleton HcRed2A. The above results indicate that protein dimerization occurs more effectively between closely linked rather than free monomers. Gel-filtration chromatography revealed similar mobility for HcRed2A and HcRed2A-tandem. Both proteins appeared to be "dimers" as evident from the similar single peaks observed between the tetrameric DsRed and monomeric EGFP peaks (data not shown). Thus, linked HcRed2A forms intramolecular but not intermolecular dimers, and may therefore be utilized as a monomeric tag for fusion partners.

To examine the properties of HcRed2A-tandem in eukaryotic cells, we fused it to cytoplasmic β-actin and nucleolar protein, fibrillarin. A series of plasmids expressing one or two copies in tandem of HcRed2A linked with actin or fibrillarin was constructed. Corresponding EGFP-tagged functional fusion proteins were used as positive controls to visualize desired fluorescent patterns. Simultaneous transient co-transfection of cells with two plasmids expressing EGFP- and HcRed2A-tagged fused constructs allowed the comparison of green and red fluorescent images within the same cells, and thus the estimation of any imperfections in the red tags used. In fusion with actin the singleton HcRed2A tag produced rather high levels of cytoplasmic aggregation within L929 fibroblasts, although some filaments and stress fibers were partially visible. In contrast, the pattern of actin structures with the HcRed2A-tandem tag was very similar to that with EGFP-actin. HcRed2A-tandem and EGFP labeling of fibers, cellular cortexes and processes were practically indistinguishable.

The differences between singleton and tandem HcRed2A tags used in conjunction with fibrillarin in HEK293 cells were not so obvious. HcRed2A-fibrillarin displayed the correct pattern in the majority of cells, although about 20% of cells still exhibited high levels of cytoplasmic red fluorescence that did not correspond to EGFP-fibrillarin distribution. On the other hand, practically all dual-color labeled cells demonstrated very similar green and red fluorescent signals in the case of HcRed2A-tandem tag. The doubled size of the tandem tag had no effect on the high-level expression in cells, proper folding of filamentous actin, and tagging to fine actin structures or the transport of fusion proteins to the nuclei. Based on these results, we conclude that the HcRed2A-tandem construct is useful for protein tagging to the same extent as EGFP.

We further applied this approach to three other tetrameric red FPs. One is DsRed2, the commercially available improved (non-aggregating and fast folding) version of DsRed. The second, HcRed, is the most far-red fluorescent mutant of the non-fluorescent chromoprotein, hcCP. The third, M355NA, is non-aggregating and the brightest red mutant of the chromoprotein asFP595 (asCP). These FPs in both singleton and tandem forms were fused to β-actin and expressed in L929 cells, together with the EGFP-actin control. As expected, all three singleton FPs displayed manifestly incorrect patterns of localization with extremely high cytoplasmic aggregation (FIG. 7). In contrast, FP-tandem proteins adequately labeled filamentous actin structures. In the latter case, the major patterns of actin structures were clearly distinguishable, although the degree of labeling and contrast between actin filaments and the background cytoplasmic signal was still lower than that in EGFP-actin images. Some non-specific aggregate formation was additionally observed with all three FP-tandems.

Recombinant DsRed2-tandem, M355NA-tandem and HcRed-tandem proteins expressed in *E. coli* were indistinguishable from their parental singletons in gel-filtration experiments, where they migrated as tetramers (data not shown). This indicates that each tandem protein molecule forms an intramolecular "dimer" consisting of two covalently linked FP-barrels, and two of these dimers combine into the "tetrameric" structure (FIG. 6C). Consequently, these tandem proteins behave as dimeric tags. This may be the main reason for the superiority of DsRed2, M355NA and HcRed tandems over singletons in protein labeling.

Taking into account the importance of fluorescence resonance energy transfer (FRET) applications, we used a simple model system to demonstrate FRET between EYFP and HcRed2A-tandem proteins. A pQE30-based plasmid encoding triple fuse HcRed2A-tandem-EYFP and containing the factor Xa protease cleavage site within the linker between the second HcRed2A and EYFP was constructed. We expected to detect spectral changes upon factor Xa digestion due to FRET elimination, analogous to the well-documented examples for pairs of GFP mutants of different colors. Indeed, incubation of purified fusion construct with factor Xa led to a gradual increase in the yellow emission peak at 528 nm and simultaneous decrease in red emission at 650 nm with an isosbestic point at 625 nm. Protease digestion resulted in an 80% increase in yellow fluorescence and 30% decrease in red fluorescence. The ratio of donor to acceptor fluorescence changed by 2.5-fold that was comparable with FRET levels between other FP pairs.

Our results indicate that the novel far-red HcRed2A-tandem may be successfully used in numerous biotechnological and cell biological applications, similarly to GFP and its mutants. This far-red tag initiates the possibility of multicolor tagging of fusion proteins that is impossible with singleton red FP tags due to the high cytoplasmic aggregation of fusion constructs. Our results show that tandem linking also improves the targeting of other red tetrameric FPs. Due to vivid spectral differences between the GFP variants used for double-labeling, the additional introduction of far-red HcRed2A-tandem together with red M355NA-tandem or DsRed2-tandem should potentially permit tetra-color applications.

Our data additionally demonstrate the usage of HcRed2A-tandem as the FRET acceptor for other FP donors, such as EYFP. This supports its application in the development of more deep tissue-penetrable far-red FRET-based assays to study in vivo protease activities and protein-protein interactions, and create intracellular sensors. Moreover, emission and excitation spectral overlays of GFP variants as well as red M355NA and far-red HcRed2A tandems should allow the simultaneous use of two independent FRET pairs of FPs in a single living cell.

C. Conclusion

In the above experiment we employed a strategy to overcome the oligomerization problem by the use of two covalently linked identical red FPs as non-oligomerizing fusion tags. We have applied this approach to the dimeric far-red fluorescent protein, HcRed2A (emission/excitation of 590/640 nm) and demonstrated its superiority in the in vivo labeling of fine cytoskeletal structures and tiny nucleoli. The resulting labeling patterns were indistinguishable from those produced by the commonly used analogous enhanced GFP (EGFP) fusion constructs. Application of this strategy to tetrameric red FPs (including DsRed2) significantly reduced the non-specific aggregation of fusion proteins and greatly improved intracellular localization. The potential use of these FP-tandem tags as acceptors for fluorescence resonance energy transfer (FRET) was demonstrated by a 2.5-times change in the emission ratio of enhanced yellow GFP mutant (EYFP) and HcRed2A-tandem FRET pair in a protease assay. HcRed2A-tandem represents the first red fluorescent tag that lacks the major drawbacks of highly oligomerizing DsRed variants and may be used safely as monomeric GFP mutants in a wide range of applications, providing distinctive far-red color.

It is evident from the above discussion and results that the subject invention provides important new mutant nucleic acid constructs encoding chromo/fluorescent proteins which find use in a variety of different applications. The subject nucleic acid constructs provide for a number of different advantages. For example, where the subject nucleic acids are employed in the production of fusion proteins, the fusion portions are tagged with fluorescent proteins that produce predictable oligomeric structures, such that precise signal to protein levels can be determined. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid encoding a polypeptide product comprising a first chromo/fluorescent domain linked by a linking domain to a second chromo/fluorescent domain, wherein said nucleic acid has a sequence identity of at least about 95% with SEQ ID NO: 05.

2. The nucleic acid according to claim 1, wherein said first and second chromo/fluorescent domains are oligomeric producing domains.

3. The nucleic acid according to claim 2, wherein said first and second chromo/fluorescent domains are chromo-or fluorescent proteins from a *Cnidarian* species.

4. The nucleic acid according to claim 3, wherein said *Cnidarian* species is a non-bioluminescent *Cnidarian* species.

5. The nucleic acid according to claim 4, wherein said non-bioluminescent *Cnidarian* species is an *Anthozoan* species.

6. The nucleic acid according to claim 1, wherein said nucleic acid encodes a fusion protein of said first and second chromo/fluorescent domains fused to a non-chromo/fluorescent protein domain.

7. A construct comprising a vector and a nucleic acid according to claim 1.

8. An expression cassette comprising:
  (a) a transcriptional initiation region functional in an expression host;
  (b) a nucleic acid according to claim 1; and
  (c) a transcriptional termination region functional in said expression host.

9. A cell, or the progeny thereof, comprising an expression cassette according to claim 8 as part of an extrachromosomal element or integrated into the genome of a host cell as a result of introduction of said expression cassette into said host cell.

10. A method of producing a polypeptide product comprising a first and second chromo/fluorescent domain, said method comprising: growing a cell according to claim 9, whereby said polypeptide product is expressed.

11. A kit comprising a nucleic acid according to claim 1.

12. A nucleic acid encoding a polypeptide product comprising a first and second *Cnidarian* chromo/fluorescent domain, wherein said first and second chromo/fluorescent domains are linked by a linking domain and wherein said nucleic acid has a sequence identity of at least about 95% with SEQ ID NO:05.

13. The nucleic acid according to claim 12, wherein said *Cnidarian* species is a non-bioluminescent *Cnidarian* species.

14. The nucleic acid according to claim 13, wherein said non-bioluminescent *Cnidarian* species is an *Anthozoan* species.

15. The nucleic acid according to claim 12, wherein said nucleic acid encodes a fusion protein of said first and second chromo/fluorescent domains fused to a non-chromo/fluorescent protein domain.

16. A construct comprising a vector and a nucleic acid according to claim 12.

17. An expression cassette comprising:
  (a) a transcriptional initiation region functional in an expression host;
  (b) a nucleic acid according to claim 12; and
  (c) a transcriptional termination region functional in said expression host.

18. A cell, or the progeny thereof, comprising an expression cassette according to claim 17 as part of an extrachromosomal element or integrated into the genome of a host cell as a result of introduction of said expression cassette into said host cell.

19. A method of producing a polypeptide product comprising a first and second chromo/fluorescent domain, said method comprising:
  growing a cell according to claim 18, whereby said polypeptide product is expressed.

20. The nucleic acid according to claim 1, wherein said linking domain is from about 1 to about 15 residues in length.

21. The nucleic acid according to claim 1, wherein said linking domain is from about 1 to about 5 residues in length.

22. The nucleic acid according to claim 12, wherein said linking domain is from about 1 to about 15 residues in length.

23. The nucleic acid according to claim 12, wherein said linking domain is from about 1 to about 5 residues in length.

* * * * *

SEQUENCE LISTING

```
<160> NUMBER OF SEQ ID NOS: 12

<210> SEQ ID NO 1
<211> LENGTH: 1396
<212> TYPE: DNA
<213> ORGANISM: Anthozoa

<400> SEQUENCE: 1
accggtcgcc accatggtga gcggcctgct gaaggagagc atgcgcatca agatgtacat      60
ggagggcacc gtgaacggcc actacttcaa gtgcgagggc gagggcgacg gcaaccccctt     120 cgccggcacc cagagcatgc ggatccacgt gaccgagggc gccccctgc ccttcgcctt       180 cgacatcctg gcccctgct gcgagtacgg cagcaggacc ttcgtgcacc acaccgccga      240
gatccccgac ttcttcaagc agagcttccc cgagggcttc acctgggaga gaaccaccac      300
ctacgaggac ggcggcatcc tgaccgccca ccaggacacc agcctggagg caactgcct      360 gatctacaag gtgaaggtgc tgggcaccaa cttccccgcc gacggccccg tgatgaagaa      420
caagagcggc ggctgggagc ccagcaccga ggtggtgtac cccgagaacg gcgtgctgtg      480
cggccggaac gtgatggccc tgaaggtggg cgaccggcgg ctgatctgcc accactacac      540
cagctaccgg agcaagaagg ccgtgcgggc cctgaccatg cccggcttcc acttcaccga      600
catccggctg cagatgctgc ggaaggagaa ggacgagtac ttcgagctgt acgaggccag      660
cgtggcccgg tacagcgacc tgcccgagaa ggccaacaga tctcccggga tggtgagcgg      720
cctgctgaag gagagcatgc gcatcaagat gtacatggag ggcaccgtga acggccacta      780
cttcaagtgc gagggcgagg gcgacggcaa ccccttcgcc ggcacccaga gcatgcggat      840
ccacgtgacc gagggcgccc ccctgccctt cgccttcgac atcctggccc cctgctgcga      900
gtacggcagc aggaccttcg tgcaccacac cgccgagatc cccgacttct tcaagcagag      960
cttccccgag ggcttcacct gggagagaac caccactac gaggacggcg gcatcctgac      1020
cgcccaccag gacaccagcc tggagggcaa ctgcctgatc tacaaggtga aggtgctggg      1080
caccaacttc cccgccgacg gccccgtgat gaagaacaag agcggcggct gggagcccag      1140
caccgaggtg gtgtacccccg agaacggcgt gctgtgcggc cggaacgtga tggccctgaa      1200
ggtgggcgac cggcggctga tctgccacca ctacaccagc taccggagca agaaggccgt      1260
gcgggccctg accatgcccg gcttccactt caccgacatc cggctgcaga tgctgcggaa      1320
ggagaaggac gagtacttcg agctgtacga ggccagcgtg gcccggtaca gcgacctgcc      1380
cgagaaggcc aactga                                                     1396

<210> SEQ ID NO 2
<211> LENGTH: 460
<212> TYPE: PRT
<213> ORGANISM: Anthozoa

<400> SEQUENCE: 2
```

-continued

```
Met Val Ser Gly Leu Leu Lys Glu Ser Met Arg Ile Lys Met Tyr Met
 1               5                  10                  15

Glu Gly Thr Val Asn Gly His Tyr Phe Lys Cys Glu Gly Glu Gly Asp
                 20                  25                  30

Gly Asn Pro Phe Ala Gly Thr Gln Ser Met Arg Ile His Val Thr Glu
             35                  40                  45

Gly Ala Pro Leu Pro Phe Ala Phe Asp Ile Leu Ala Pro Cys Cys Glu
 50                  55                  60

Tyr Gly Ser Arg Thr Phe Val His His Thr Ala Glu Ile Pro Asp Phe
 65                  70                  75                  80

Phe Lys Gln Ser Phe Pro Glu Gly Phe Thr Trp Glu Arg Thr Thr Thr
                 85                  90                  95

Tyr Glu Asp Gly Gly Ile Leu Thr Ala His Gln Asp Thr Ser Leu Glu
                100                 105                 110

Gly Asn Cys Leu Ile Tyr Lys Val Lys Val Leu Gly Thr Asn Phe Pro
                115                 120                 125

Ala Asp Gly Pro Val Met Lys Asn Lys Ser Gly Gly Trp Glu Pro Ser
130                 135                 140

Thr Glu Val Val Tyr Pro Glu Asn Gly Val Leu Cys Gly Arg Asn Val
145                 150                 155                 160

Met Ala Leu Lys Val Gly Asp Arg Arg Leu Ile Cys His His Tyr Thr
                165                 170                 175

Ser Tyr Arg Ser Lys Lys Ala Val Arg Ala Leu Thr Met Pro Gly Phe
                180                 185                 190

His Phe Thr Asp Ile Arg Leu Gln Met Leu Arg Lys Glu Lys Asp Glu
                195                 200                 205

Tyr Phe Glu Leu Tyr Glu Ala Ser Val Ala Arg Tyr Ser Asp Leu Pro
                210                 215                 220

Glu Lys Ala Asn Arg Ser Pro Gly Met Val Ser Gly Leu Leu Lys Glu
225                 230                 235                 240

Ser Met Arg Ile Lys Met Tyr Met Glu Gly Thr Val Asn Gly His Tyr
                245                 250                 255

Phe Lys Cys Glu Gly Glu Gly Asp Gly Asn Pro Phe Ala Gly Thr Gln
                260                 265                 270

Ser Met Arg Ile His Val Thr Glu Gly Ala Pro Leu Pro Phe Ala Phe
                275                 280                 285

Asp Ile Leu Ala Pro Cys Cys Glu Tyr Gly Ser Arg Thr Phe Val His
290                 295                 300

His Thr Ala Glu Ile Pro Asp Phe Phe Lys Gln Ser Phe Pro Glu Gly
305                 310                 315                 320

Phe Thr Trp Glu Arg Thr Thr Thr Tyr Glu Asp Gly Gly Ile Leu Thr
                325                 330                 335

Ala His Gln Asp Thr Ser Leu Glu Gly Asn Cys Leu Ile Tyr Lys Val
                340                 345                 350

Lys Val Leu Gly Thr Asn Phe Pro Ala Asp Gly Pro Val Met Lys Asn
                355                 360                 365

Lys Ser Gly Gly Trp Glu Pro Ser Thr Glu Val Val Tyr Pro Glu Asn
                370                 375                 380

Gly Val Leu Cys Gly Arg Asn Val Met Ala Leu Lys Val Gly Asp Arg
385                 390                 395                 400

Arg Leu Ile Cys His His Tyr Thr Ser Tyr Arg Ser Lys Lys Ala Val
                405                 410                 415

Arg Ala Leu Thr Met Pro Gly Phe His Phe Thr Asp Ile Arg Leu Gln
```

```
                420            425            430
Met Leu Arg Lys Glu Lys Asp Glu Tyr Phe Glu Leu Tyr Glu Ala Ser
        435                440                445

Val Ala Arg Tyr Ser Asp Leu Pro Glu Lys Ala Asn
    450                455                460

<210> SEQ ID NO 3
<211> LENGTH: 1424
<212> TYPE: DNA
<213> ORGANISM: Anthozoa

<400> SEQUENCE: 3
accggtcgcc accatggtga gcggcctgct gaaggagagc atgcgcatca agatgtacat     60
ggagggcacc gtgaacggcc actacttcaa gtgcgagggc gagggcgacg gcaacccctt    120
cgccggcacc cagagcatgc ggatccacgt gaccgagggc gccccctgc ccttcgcctt     180
cgacatcctg gcccctgct gcgagtacgg cagcaggacc ttcgtgcacc acaccgccga    240
gatccccgac ttcttcaagc agagcttccc cgagggcttc acctgggaga gaaccaccac    300
ctacgaggac ggcggcatcc tgaccgccca ccaggacacc agcctggagg caactgcct    360
gatctacaag gtgaaggtgc tgggcaccaa cttccccgcc gacggccccg tgatgaagaa    420
caagagcggc ggctgggagc ccagcaccga ggtggtgtac cccgagaacg cgtgctgtg    480
cggccggaac gtgatggccc tgaaggtggg cgaccggcgg ctgatctgcc accactacac    540
cagctaccgg agcaagaagg ccgtgcgggc cctgaccatg cccggcttcc acttcaccga    600
catccggctg cagatgctgc ggaaggagaa ggacgagtac ttcgagctgt acgaggccag    660
cgtggcccgg tacagcgacc tgcccgagaa ggccaacaga tctcccggga tggtgagcgg    720
cctgctgaag gagagcatgc gcatcaagat gtacatggag ggcaccgtga acggccacta    780
cttcaagtgc gagggcgagg cgacggcaa ccccttcgcc ggcacccaga gcatgcggat    840
ccacgtgacc gagggcgccc cctgcccttt cgccttcgac atcctggccc ctgctgcga    900
gtacggcagc aggaccttcg tgcaccacac cgccgagatc cccgacttct tcaagcagag    960
cttccccgag ggcttcacct gggagagaac caccacctac gaggacggcg gcatcctgac   1020
cgccaccag gacaccagcc tggagggcaa ctgcctgatc tacaaggtga aggtgctggg   1080
caccaacttc cccgccgacg gccccgtgat gaagaacaag agcggcggct gggagcccag   1140
caccgaggtg gtgtaccccg agaacggcgt gctgtgcggc cggaacgtga tggccctgaa   1200
ggtgggcgac cggcggctga tctgccacca ctacaccagc taccggagca agaaggccgt   1260
gcgggccctg accatgcccg gcttccactt caccgacatc cggctgcaga tgctgcggaa   1320
ggagaaggac gagtacttcg agctgtacga ggccagcgtg gcccggtaca gcgacctgcc   1380
cgagaaggcc aacagaactc gagctatgga tgatgatatc gccg                    1424

<210> SEQ ID NO 4
<211> LENGTH: 470
<212> TYPE: PRT
<213> ORGANISM: Anthozoa

<400> SEQUENCE: 4

Met Val Ser Gly Leu Leu Lys Glu Ser Met Arg Ile Lys Met Tyr Met
 1               5                  10                  15

Glu Gly Thr Val Asn Gly His Tyr Phe Lys Cys Glu Gly Glu Gly Asp
            20                  25                  30

Gly Asn Pro Phe Ala Gly Thr Gln Ser Met Arg Ile His Val Thr Glu
```

```
                  35                  40                  45
Gly Ala Pro Leu Pro Phe Ala Phe Asp Ile Leu Ala Pro Cys Cys Glu
                 50                  55                  60

Tyr Gly Ser Arg Thr Phe Val His His Thr Ala Glu Ile Pro Asp Phe
 65                  70                  75                  80

Phe Lys Gln Ser Phe Pro Glu Gly Phe Thr Trp Glu Arg Thr Thr Thr
                 85                  90                  95

Tyr Glu Asp Gly Gly Ile Leu Thr Ala His Gln Asp Thr Ser Leu Glu
                100                 105                 110

Gly Asn Cys Leu Ile Tyr Lys Val Lys Val Leu Gly Thr Asn Phe Pro
                115                 120                 125

Ala Asp Gly Pro Val Met Lys Asn Lys Ser Gly Gly Trp Glu Pro Ser
            130                 135                 140

Thr Glu Val Val Tyr Pro Glu Asn Gly Val Leu Cys Gly Arg Asn Val
145                 150                 155                 160

Met Ala Leu Lys Val Gly Asp Arg Arg Leu Ile Cys His His Tyr Thr
                165                 170                 175

Ser Tyr Arg Ser Lys Lys Ala Val Arg Ala Leu Thr Met Pro Gly Phe
            180                 185                 190

His Phe Thr Asp Ile Arg Leu Gln Met Leu Arg Lys Glu Lys Asp Glu
            195                 200                 205

Tyr Phe Glu Leu Tyr Glu Ala Ser Val Ala Arg Tyr Ser Asp Leu Pro
            210                 215                 220

Glu Lys Ala Asn Arg Ser Pro Gly Met Val Ser Gly Leu Leu Lys Glu
225                 230                 235                 240

Ser Met Arg Ile Lys Met Tyr Met Glu Gly Thr Val Asn Gly His Tyr
                245                 250                 255

Phe Lys Cys Glu Gly Glu Gly Asp Gly Asn Pro Phe Ala Gly Thr Gln
                260                 265                 270

Ser Met Arg Ile His Val Thr Glu Gly Ala Pro Leu Pro Phe Ala Phe
            275                 280                 285

Asp Ile Leu Ala Pro Cys Cys Glu Tyr Gly Ser Arg Thr Phe Val His
        290                 295                 300

His Thr Ala Glu Ile Pro Asp Phe Phe Lys Gln Ser Phe Pro Glu Gly
305                 310                 315                 320

Phe Thr Trp Glu Arg Thr Thr Thr Tyr Glu Asp Gly Gly Ile Leu Thr
                325                 330                 335

Ala His Gln Asp Thr Ser Leu Glu Gly Asn Cys Leu Ile Tyr Lys Val
            340                 345                 350

Lys Val Leu Gly Thr Asn Phe Pro Ala Asp Gly Pro Val Met Lys Asn
            355                 360                 365

Lys Ser Gly Gly Trp Glu Pro Ser Thr Glu Val Val Tyr Pro Glu Asn
        370                 375                 380

Gly Val Leu Cys Gly Arg Asn Val Met Ala Leu Lys Val Gly Asp Arg
385                 390                 395                 400

Arg Leu Ile Cys His His Tyr Thr Ser Tyr Arg Ser Lys Lys Ala Val
                405                 410                 415

Arg Ala Leu Thr Met Pro Gly Phe His Phe Thr Asp Ile Arg Leu Gln
            420                 425                 430

Met Leu Arg Lys Glu Lys Asp Glu Tyr Phe Glu Leu Tyr Glu Ala Ser
        435                 440                 445

Val Ala Arg Tyr Ser Asp Leu Pro Glu Lys Ala Asn Arg Thr Arg Ala
    450                 455                 460
```

Met Asp Asp Asp Ile Ala
465                 470

<210> SEQ ID NO 5
<211> LENGTH: 1376
<212> TYPE: DNA
<213> ORGANISM: Anthozoa

<400> SEQUENCE: 5

| | | | | | |
|---|---|---|---|---|---|
| atgtctggtt | tgttgaaaga | aagtatgcgc | atcaagatgt | acatggaagg | cacggttaat | 60 |
| ggccattatt | tcaagtgtga | aggagaggga | gacggcaacc | catttgcagg | tacgcagagc | 120 |
| atgaggattc | atgtcaccga | agggctcca | ttaccatttg | ccttcgacat | tttggcaccg | 180 |
| tgttgtgagt | acggcagcag | gacctttgtc | caccatacgg | cagagattcc | cgatttcttc | 240 |
| aagcagtctt | tccctgaagg | ctttacttgg | aaagaacca | caacctatga | agatggaggc | 300 |
| attcttactg | ctcatcagga | cacaagcctg | gaggggaact | gccttatata | caaggtgaaa | 360 |
| gtccatggta | ccaattttcc | tgctgatggc | cccgtgatga | agaacaaatc | aggaggatgg | 420 |
| gagccaagca | ctgaggtggt | ttatccagag | aatggtgtcc | tgtgtggacg | taatgtgatg | 480 |
| gcccttaaag | tcggtgatcg | tcatttgatc | tgccatcact | atacttctta | caggtccaag | 540 |
| aaagcagtcc | gtgccttgac | aatgccagga | tttcatttta | cagacatccg | ccttcagatg | 600 |
| ctgaggaaaa | agaaagacga | gtactttgaa | ctgtacgaag | catctgtggc | taggtacagt | 660 |
| gatcttcctg | aaaagcaaa | agatctcccg | ggatgtctgg | tttgttgaaa | gaaagtatgc | 720 |
| gcatcaagat | gtacatggaa | ggcacggtta | atggccatta | tttcaagtgt | gaaggagagg | 780 |
| gagacggcaa | cccatttgca | ggtacgcaga | gcatgaggat | tcatgtcacc | gaaggggctc | 840 |
| cattaccatt | tgccttcgac | attttggcac | cgtgttgtga | gtacggcagc | aggacctttg | 900 |
| tccaccatac | ggcagagatt | cccgatttct | tcaagcagtc | tttccctgaa | ggctttactt | 960 |
| gggaaagaac | cacaacctat | gaagatggag | gcattcttac | tgctcatcag | gacacaagcc | 1020 |
| tggaggggaa | ctgccttata | tacaaggtga | agtccatgg | taccaatttt | cctgctgatg | 1080 |
| gccccgtgat | gaagaacaaa | tcaggaggat | gggagccaag | cactgaggtg | gtttatccag | 1140 |
| agaatggtgt | cctgtgtgga | cgtaatgtga | tggcccttaa | agtcggtgat | cgtcatttga | 1200 |
| tctgccatca | ctatacttct | tacaggtcca | agaaagcagt | ccgtgccttg | acaatgccag | 1260 |
| gatttcattt | tacagacatc | cgccttcaga | tgctgaggaa | aaagaaagac | gagtactttg | 1320 |
| aactgtacga | agcatctgtg | gctaggtaca | gtgatcttcc | tgaaaagca | aattga | 1376 |

<210> SEQ ID NO 6
<211> LENGTH: 458
<212> TYPE: PRT
<213> ORGANISM: Anthozoa

<400> SEQUENCE: 6

Met Ser Gly Leu Leu Lys Glu Ser Met Arg Ile Lys Met Tyr Met Glu
1               5                   10                  15

Gly Thr Val Asn Gly His Tyr Phe Lys Cys Glu Gly Glu Gly Asp Gly
            20                  25                  30

Asn Pro Phe Ala Gly Thr Gln Ser Met Arg Ile His Val Thr Glu Gly
        35                  40                  45

Ala Pro Leu Pro Phe Ala Phe Asp Ile Leu Ala Pro Cys Cys Glu Tyr
    50                  55                  60

Gly Ser Arg Thr Phe Val His His Thr Ala Glu Ile Pro Asp Phe Phe

```
            65                  70                  75                  80
Lys Gln Ser Phe Pro Glu Gly Phe Thr Trp Glu Arg Thr Thr Thr Tyr
                    85                  90                  95

Glu Asp Gly Gly Ile Leu Thr Ala His Gln Asp Thr Ser Leu Glu Gly
                100                 105                 110

Asn Cys Leu Ile Tyr Lys Val Lys Val His Gly Thr Asn Phe Pro Ala
                115                 120                 125

Asp Gly Pro Val Met Lys Asn Lys Ser Gly Gly Trp Glu Pro Ser Thr
            130                 135                 140

Glu Val Val Tyr Pro Glu Asn Gly Val Leu Cys Gly Arg Asn Val Met
145                 150                 155                 160

Ala Leu Lys Val Gly Asp Arg His Leu Ile Cys His His Tyr Thr Ser
                165                 170                 175

Tyr Arg Ser Lys Lys Ala Val Arg Ala Leu Thr Met Pro Gly Phe His
                180                 185                 190

Phe Thr Asp Ile Arg Leu Gln Met Leu Arg Lys Lys Asp Glu Tyr
                195                 200                 205

Phe Glu Leu Tyr Glu Ala Ser Val Ala Arg Tyr Ser Asp Leu Pro Glu
            210                 215                 220

Lys Ala Asn Arg Ser Pro Gly Met Ser Gly Leu Leu Lys Glu Ser Met
225                 230                 235                 240

Arg Ile Lys Met Tyr Met Glu Gly Thr Val Asn Gly His Tyr Phe Lys
                245                 250                 255

Cys Glu Gly Glu Gly Asp Gly Asn Pro Phe Ala Gly Thr Gln Ser Met
                260                 265                 270

Arg Ile His Val Thr Glu Gly Ala Pro Leu Pro Phe Ala Phe Asp Ile
            275                 280                 285

Leu Ala Pro Cys Cys Glu Tyr Gly Ser Arg Thr Phe Val His His Thr
290                 295                 300

Ala Glu Ile Pro Asp Phe Phe Lys Gln Ser Phe Pro Glu Gly Phe Thr
305                 310                 315                 320

Trp Glu Arg Thr Thr Thr Tyr Glu Asp Gly Gly Ile Leu Thr Ala His
                325                 330                 335

Gln Asp Thr Ser Leu Glu Gly Asn Cys Leu Ile Tyr Lys Val Lys Val
            340                 345                 350

His Gly Thr Asn Phe Pro Ala Asp Gly Pro Val Met Lys Asn Lys Ser
            355                 360                 365

Gly Gly Trp Glu Pro Ser Thr Glu Val Val Tyr Pro Glu Asn Gly Val
        370                 375                 380

Leu Cys Gly Arg Asn Val Met Ala Leu Lys Val Gly Asp Arg His Leu
385                 390                 395                 400

Ile Cys His His Tyr Thr Ser Tyr Arg Ser Lys Lys Ala Val Arg Ala
                405                 410                 415

Leu Thr Met Pro Gly Phe His Phe Thr Asp Ile Arg Leu Gln Met Leu
            420                 425                 430

Arg Lys Lys Asp Glu Tyr Phe Glu Leu Tyr Glu Ala Ser Val Ala
        435                 440                 445

Arg Tyr Ser Asp Leu Pro Glu Lys Ala Asn
    450                 455

<210> SEQ ID NO 7
<211> LENGTH: 1404
<212> TYPE: DNA
<213> ORGANISM: anthozoa
```

<400> SEQUENCE: 7

```
atggcctccc tgctgaccga gaccatgccc ttcaggacca ccatcgaggg caccgtgaac    60
ggccactact tcaagtgcac cggcaagggc gagggcaacc ccctcgaggg cacccaggag   120
atgaagatcg aggtgatcga gggcggcccc ctgcccttcg ccttccacat cctgtccacc   180
tcctgcatgt acggctccaa ggccttcatc aagtacgtgt ccggcatccc cgactacttc   240
aagcagtccc tccccgaggg cttcacctgg agcgcaccac ccacctacga ggacggcggc   300
ttcctgaccg cccaccagga cacctccctg gacggcgact gcctggtgta caaggtgaag   360
atcctgggca caacttcccc cgccgacggc cccgtgatgc agaacaaggc cggccgctgg   420
gagccctcca ccgagatcgt gtacgaggtg acggcgtgc tgcgcggcca gtccagcatg   480
gccctggagt gccccggcgg tcgccacctg acctgccacc tgcacaccac ctaccgctcc   540
aagaagcccg cctccgccct gaagatgccc ggcttccact cgaggacca ccgcatcgag    600
atcctggagg aggtggagaa gggcaagtgc tacaagcagt acgaggccgc cgtgggccgc   660
tactgcgacg ccgcccccctc caagctgggc acaacagat ctcccgggat ggcctccctg   720
ctgaccgaga ccatgccctt caggaccacc atcgagggca ccgtgaacgg ccactacttc   780
aagtgcaccg gcaagggcga gggcaacccc ctcgagggca ccaggagat gaagatcgag    840
gtgatcgagg gcggccccct gcccttcgcc ttccacatcc tgtccacctc ctgcatgtac   900
ggctccaagg ccttcatcaa gtacgtgtcc ggcatcccccg actacttcaa gcagtccctc   960
cccgagggct tcacctggga gcgcaccacc acctacgagg acggcggctt cctgaccgcc  1020
caccaggaca cctccctgga cggcgactgc ctggtgtaca aggtgaagat cctgggcaac  1080
aacttccccg ccgacggccc cgtgatgcag aacaaggccg ccgctggga gccctccacc   1140
gagatcgtgt acgaggtgga cggcgtgctg cgcggccagt ccagcatggc cctggagtgc  1200
cccggcggtc gccacctgac ctgccacctg cacaccacct accgctccaa gaagcccgcc  1260
tccgccctga agatgcccgg cttccacttc gaggaccacc gcatcgagat cctggaggag  1320
gtggagaagg gcaagtgcta caagcagtac gaggccgccg tgggccgcta ctgcgacgcc  1380
gccccctcca agctgggcca caac                                         1404
```

<210> SEQ ID NO 8
<211> LENGTH: 468
<212> TYPE: PRT
<213> ORGANISM: Anthozoa

<400> SEQUENCE: 8

```
Met Ala Ser Leu Leu Thr Glu Thr Met Pro Phe Arg Thr Thr Ile Glu
  1               5                  10                  15

Gly Thr Val Asn Gly His Tyr Phe Lys Cys Thr Gly Lys Gly Glu Gly
             20                  25                  30

Asn Pro Leu Glu Gly Thr Gln Glu Met Lys Ile Glu Val Ile Glu Gly
         35                  40                  45

Gly Pro Leu Pro Phe Ala Phe His Ile Leu Ser Thr Ser Cys Met Tyr
     50                  55                  60

Gly Ser Lys Ala Phe Ile Lys Tyr Val Ser Gly Ile Pro Asp Tyr Phe
 65                  70                  75                  80

Lys Gln Ser Leu Pro Glu Gly Phe Thr Trp Glu Arg Thr Thr Thr Tyr
                 85                  90                  95

Glu Asp Gly Gly Phe Leu Thr Ala His Gln Asp Thr Ser Leu Asp Gly
            100                 105                 110
```

```
Asp Cys Leu Val Tyr Lys Val Lys Ile Leu Gly Asn Asn Phe Pro Ala
        115                 120                 125

Asp Gly Pro Val Met Gln Asn Lys Ala Gly Arg Trp Glu Pro Ser Thr
    130                 135                 140

Glu Ile Val Tyr Glu Val Asp Gly Val Leu Arg Gly Gln Ser Ser Met
145                 150                 155                 160

Ala Leu Glu Cys Pro Gly Gly Arg His Leu Thr Cys His Leu His Thr
                165                 170                 175

Thr Tyr Arg Ser Lys Lys Pro Ala Ser Ala Leu Lys Met Pro Gly Phe
                180                 185                 190

His Phe Glu Asp His Arg Ile Glu Ile Leu Glu Glu Val Glu Lys Gly
            195                 200                 205

Lys Cys Tyr Lys Gln Tyr Glu Ala Ala Val Gly Arg Tyr Cys Asp Ala
        210                 215                 220

Ala Pro Ser Lys Leu Gly His Asn Arg Ser Pro Gly Met Ala Ser Leu
225                 230                 235                 240

Leu Thr Glu Thr Met Pro Phe Arg Thr Thr Ile Glu Gly Thr Val Asn
                245                 250                 255

Gly His Tyr Phe Lys Cys Thr Gly Lys Gly Glu Gly Asn Pro Leu Glu
                260                 265                 270

Gly Thr Gln Glu Met Lys Ile Glu Val Ile Glu Gly Gly Pro Leu Pro
            275                 280                 285

Phe Ala Phe His Ile Leu Ser Thr Ser Cys Met Tyr Gly Ser Lys Ala
290                 295                 300

Phe Ile Lys Tyr Val Ser Gly Ile Pro Asp Tyr Phe Lys Gln Ser Leu
305                 310                 315                 320

Pro Glu Gly Phe Thr Trp Glu Arg Thr Thr Thr Tyr Glu Asp Gly Gly
                325                 330                 335

Phe Leu Thr Ala His Gln Asp Thr Ser Leu Asp Gly Asp Cys Leu Val
                340                 345                 350

Tyr Lys Val Lys Ile Leu Gly Asn Asn Phe Pro Ala Asp Gly Pro Val
                355                 360                 365

Met Gln Asn Lys Ala Gly Arg Trp Glu Pro Ser Thr Glu Ile Val Tyr
    370                 375                 380

Glu Val Asp Gly Val Leu Arg Gly Gln Ser Ser Met Ala Leu Glu Cys
385                 390                 395                 400

Pro Gly Gly Arg His Leu Thr Cys His Leu His Thr Thr Tyr Arg Ser
                405                 410                 415

Lys Lys Pro Ala Ser Ala Leu Lys Met Pro Gly Phe His Phe Glu Asp
                420                 425                 430

His Arg Ile Glu Ile Leu Glu Glu Val Glu Lys Gly Lys Cys Tyr Lys
            435                 440                 445

Gln Tyr Glu Ala Ala Val Gly Arg Tyr Cys Asp Ala Ala Pro Ser Lys
        450                 455                 460

Leu Gly His Asn
465
```

<210> SEQ ID NO 9
<211> LENGTH: 1398
<212> TYPE: DNA
<213> ORGANISM: Anthozoa

<400> SEQUENCE: 9
gcctccctgc tgaccgagac catgcccttc aggaccacca tcgagggcac cgtgaacggc      60

```
cactacttca agtgcaccgg caagggcgag ggcaaccccc tcgagggcac ccaggagatg      120
aagatcgagg tgatcgaggg cggccccctg cccttcgcct tccacatcct gtccacctcc      180
tgcatgtacg gctccaaggc cttcatcaag tacgtgtccg gcatccccga ctacttcaag      240
cagtccctcc ccgagggctt cacctgggag cgcaccacca cctacgagga cggcggcttc      300
ctgaccgccc accaggacac ctccctggac ggcgactgcc tggtgtacaa ggtgaagatc      360
ctgggcaaca acttccccgc cgacggcccc gtgatgcaga caaggccgg ccgctgggag       420 ccctccaccg agatcgtgta cgaggtggac ggcgtgctgc gcggccagtc cctgatggcc      480
ctggagtgcc ccggcggtcg ccacctgacc tgccacctgc acaccaccta ccgctccaag      540
aagcccgcct ccgccctgaa gatgcccggc ttccacttcg aggaccaccg catcgagatc      600
ctggaggagg tggagaaggg caagtgctac aagcagtacg aggccgccgt gggccgctac      660
tgcgacgccg ccccctccaa gctgggccac aacagatctc ccggggcctc cctgctgacc      720
gagaccatgc ccttcaggac caccatcgag ggcaccgtga cggccacta cttcaagtgc       780 accggcaagg gcgagggcaa ccccctcgag ggcacccagg agatgaagat cgaggtgatc      840
gagggcggcc ccctgccctt cgccttccac atcctgtcca cctcctgcat gtacggctcc      900
aaggccttca tcaagtacgt gtccggcatc cccgactact tcaagcagtc cctccccgag      960
ggcttcacct gggagcgcac caccacctac gaggacggcg gcttcctgac cgcccaccag     1020
gacacctccc tggacggcga ctgcctggta tacaaggtga gatcctggg caacaacttc      1080 cccgccgacg gccccgtgat gcagaacaag gccggccgct gggagccctc caccgagatc     1140
gtgtacgagg tggacggcgt gctgcgcggc cagtccctga tggccctgga gtgccccggc     1200
ggtcgccacc tgacctgcca cctgcacacc acctaccgct ccaagaagcc cgcctccgcc     1260
ctgaagatgc ccggcttcca cttcgaggac caccgcatcg agatcctgga ggaggtggag     1320
aagggcaagt gctacaagca gtacgaggcc gccgtgggcc gctactgcga cgccgccccc     1380
tccaagctgg gccacaac                                                  1398
```

<210> SEQ ID NO 10
<211> LENGTH: 466
<212> TYPE: PRT
<213> ORGANISM: Anthozoa

<400> SEQUENCE: 10

```
Ala Ser Leu Leu Thr Glu Thr Met Pro Phe Arg Thr Thr Ile Glu Gly
 1               5                  10                  15

Thr Val Asn Gly His Tyr Phe Lys Cys Thr Gly Lys Gly Glu Gly Asn
            20                  25                  30

Pro Leu Glu Gly Thr Gln Glu Met Lys Ile Glu Val Ile Glu Gly Gly
        35                  40                  45

Pro Leu Pro Phe Ala Phe His Ile Leu Ser Thr Ser Cys Met Tyr Gly
    50                  55                  60

Ser Lys Ala Phe Ile Lys Tyr Val Ser Gly Ile Pro Asp Tyr Phe Lys
65                  70                  75                  80

Gln Ser Leu Pro Glu Gly Phe Thr Trp Glu Arg Thr Thr Thr Tyr Glu
                85                  90                  95

Asp Gly Gly Phe Leu Thr Ala His Gln Asp Thr Ser Leu Asp Gly Asp
            100                 105                 110

Cys Leu Val Tyr Lys Val Lys Ile Leu Gly Asn Asn Phe Pro Ala Asp
        115                 120                 125
```

-continued

```
Gly Pro Val Met Gln Asn Lys Ala Gly Arg Trp Glu Pro Ser Thr Glu
    130                 135                 140
Ile Val Tyr Glu Val Asp Gly Val Leu Arg Gly Gln Ser Leu Met Ala
145                 150                 155                 160
Leu Glu Cys Pro Gly Gly Arg His Leu Thr Cys His Leu His Thr Thr
                165                 170                 175
Tyr Arg Ser Lys Lys Pro Ala Ser Ala Leu Lys Met Pro Gly Phe His
            180                 185                 190
Phe Glu Asp His Arg Ile Glu Ile Leu Glu Glu Val Glu Lys Gly Lys
        195                 200                 205
Cys Tyr Lys Gln Tyr Glu Ala Ala Val Gly Arg Tyr Cys Asp Ala Ala
    210                 215                 220
Pro Ser Lys Leu Gly His Asn Arg Ser Pro Gly Ala Ser Leu Leu Thr
225                 230                 235                 240
Glu Thr Met Pro Phe Arg Thr Thr Ile Glu Gly Thr Val Asn Gly His
                245                 250                 255
Tyr Phe Lys Cys Thr Gly Lys Gly Glu Gly Asn Pro Leu Glu Gly Thr
            260                 265                 270
Gln Glu Met Lys Ile Glu Val Ile Glu Gly Gly Pro Leu Pro Phe Ala
        275                 280                 285
Phe His Ile Leu Ser Thr Ser Cys Met Tyr Gly Ser Lys Ala Phe Ile
    290                 295                 300
Lys Tyr Val Ser Gly Ile Pro Asp Tyr Phe Lys Gln Ser Leu Pro Glu
305                 310                 315                 320
Gly Phe Thr Trp Glu Arg Thr Thr Tyr Glu Asp Gly Gly Phe Leu
                325                 330                 335
Thr Ala His Gln Asp Thr Ser Leu Asp Gly Asp Cys Leu Val Tyr Lys
            340                 345                 350
Val Lys Ile Leu Gly Asn Asn Phe Pro Ala Asp Gly Pro Val Met Gln
        355                 360                 365
Asn Lys Ala Gly Arg Trp Glu Pro Ser Thr Glu Ile Val Tyr Glu Val
    370                 375                 380
Asp Gly Val Leu Arg Gly Gln Ser Leu Met Ala Leu Glu Cys Pro Gly
385                 390                 395                 400
Gly Arg His Leu Thr Cys His Leu His Thr Thr Tyr Arg Ser Lys Lys
                405                 410                 415
Pro Ala Ser Ala Leu Lys Met Pro Gly Phe His Phe Glu Asp His Arg
            420                 425                 430
Ile Glu Ile Leu Glu Glu Val Glu Lys Gly Lys Cys Tyr Lys Gln Tyr
        435                 440                 445
Glu Ala Ala Val Gly Arg Tyr Cys Asp Ala Ala Pro Ser Lys Leu Gly
    450                 455                 460
His Asn
465
```

<210> SEQ ID NO 11
<211> LENGTH: 29
<212> TYPE: DNA
<213> ORGANISM: human

<400> SEQUENCE: 11
ggtgctcgag ccatgaagcc aggattcag                                29

<210> SEQ ID NO 12
<211> LENGTH: 30

-continued

```
<212> TYPE: DNA
<213> ORGANISM: human

<400> SEQUENCE: 12
ggtgggatcc tcagttcttc accttgggggg                               30
```